United States Patent
Shenoy et al.

(10) Patent No.: US 6,731,964 B2
(45) Date of Patent: May 4, 2004

(54) PROCESSED NEURAL SIGNALS AND METHODS FOR GENERATING AND USING THEM

(75) Inventors: Krishna V. Shenoy, Los Angeles, CA (US); Richard A. Andersen, La Canada, CA (US); Sohaib A. Kureshi, Chapel Hill, NC (US)

(73) Assignee: California Institute of Technology, Pasadena, CA (US)

( * ) Notice: Subject to any disclaimer, the term of this patent is extended or adjusted under 35 U.S.C. 154(b) by 0 days.

(21) Appl. No.: 10/216,668

(22) Filed: Aug. 9, 2002

(65) Prior Publication Data

US 2003/0050569 A1 Mar. 13, 2003

Related U.S. Application Data

(63) Continuation of application No. 09/369,953, filed on Aug. 6, 1999, now Pat. No. 6,609,017.
(60) Provisional application No. 60/099,222, filed on Sep. 4, 1998, and provisional application No. 60/095,833, filed on Aug. 7, 1998.

(51) Int. Cl.$^7$ ................................................. A61B 5/04
(52) U.S. Cl. ........................ 600/372; 600/378; 600/544
(58) Field of Search ................................. 600/544, 545, 600/372, 378

(56) References Cited

U.S. PATENT DOCUMENTS

| | | | | |
|---|---|---|---|---|
| 4,878,913 A | * | 11/1989 | Aebischer et al. | 623/12 |
| 5,178,161 A | * | 1/1993 | Kovacs | 600/378 |
| 6,171,239 B1 | * | 1/2001 | Humphrey | 600/372 |
| 6,609,017 B1 | * | 8/2003 | Shenoy et al. | 600/372 |
| 6,615,076 B2 | * | 9/2003 | Mitra et al. | 600/544 |

OTHER PUBLICATIONS

Aaron P. Batista et al, "Reach Plan in Eye Centered Coordinates," Science, Jul. 9, 1999, vol 285, pp. /257–260.*
Haugland et al, "Artifact Free Sensory Nerve Signals Obtained from Cuff Electrodes During Electrical Stimulation of Nearby Muscles," IEEE Transactions on Rehabilitation Engineering, vol. 2, No. 1, Mar. 1994, pp. 37–40.*
W. Wayt Gibbs, "Mind Readings, "Scientific American, Vol 74, No. 1. Jun. 1996, pp. 34–36.*
Dr. Richard K. Eisley, "Adaptive Control of Prosthetic Limbs Using Neural Networks," IJCNN Joint Conference on Neural Networks, 1990, pp. II–771–776.*
Eisley et al, "Appluication of Neural Networks to Adaptive Control", 1988.*
Mountcastle, V.B. et al., "Posterior Parietal Association Cortex of the Monkey: Command Functions for Operations Within Extrapersonal Space," *Journal of Neurophysiology*, Jul 1975, 38(4):871–908. (Exhibit 13).
Salinas, Emilio and L. F. Abbott, "Transfer of Coded Information from Sensory to Motor Networks," *The Journal of Neuroscience*, Oct. 1995, 15(10):6461–74. (Exhibit 14).
Salinas, Emilio and L. F. Abbott, "Vector Reconstruction from Firing Rates," *Journal of Computational Neuroscience*, 1994, 1:89–107. (Exhibit 15).
Schwartz, Andrew B., "Motor Cortical Activity During Drawing Movements: Population Representation During Sinusoid Tracing," *Journal of Neurophysiology*, Jul. 1993, 70(1):28–36. (Exhibit 16).

(List continued on next page.)

*Primary Examiner*—Robert L. Nasser
(74) *Attorney, Agent, or Firm*—Fish & Richardson P.C.

(57) ABSTRACT

The present invention provides a processed neural signal that encodes a reach plan, comprising the target location of the planned reach encoded relative to an eye-centered reference frame. The present invention also provides methods for generating and decoding the processed neural signal.

36 Claims, 9 Drawing Sheets

OTHER PUBLICATIONS

Snyder, L. H. et al., "Coding of Intention in the Posterior Parietal Cortex," *Nature*, Mar. 13, 1997, 386:167–70. (Exhibit 17).

Zhang, Kechen et al., "Interpreting Neuronal Population Activity by Reconstruction: Unified Framework with Application to Hippocampal Place Cells," *Journal of Neurophysiology*, Feb. 1998, 79(2):1017–1044. (Exhibit 18).

Zipser, David and Richard A. Andersen, "A Back–Propagation Programmed Network that Simulates Response Properties of a Subset of Posterior Parietal Neurons," *Nature*, Feb. 25, 1988, 331(6158):679–84. (Exhibit 19).

Brown, Emery N. et al., "A Statistical Paradigm for Neural Spike Train Decoding Applied to Position Prediction from Ensemble Firing Patterns of Rat Hippocampal Place Cells," *The Journal of Neuroscience*, Sep. 15, 1998, 18(18):7411–25. (Exhibit 1).

Buonomano, Dean V. and Michael M. Merzenich, "Cortical Plasticity: From Synapses to Maps," *Annual Review of Neuroscience*, 1998, 21:49–86. (Exhibit 2).

Colby, Carol L., "Action–Oriented Spatial Reference Frames in Corte x," *Neuron*, Jan. 1998, 20:15–24. (Exhibit 3).

Colby, Carol L. and Jean–René Duhamel, "Heterogeneity of Extrastriate Visual Areas and Multiple Parietal Areas in the Macaque Monkey," *Neurophychologia*, 1991, 29(6):517–37. (Exhibit 4).

Clower, Dottie M. et al., "Role of Posterior Parietal Cortex in the Recalibration of Visually Guided Reaching," *Nature*, Oct. 17, 1996, 383(6601):618–21. (Exhibit 5).

Galleti, C. et al., "Short Communication Arm Movement–related Neurons in the Visual Area V6A of the Macaque Superior Parietal Lobule," *European Journal of Neuroscience*, Feb. 1997, 9(2):410–3.

Grinvald, Amiram et al., "High–Resolution Optical Imaging of Functional Brain Architecture in the Awake Monkey (Behaving Monkey / Ocular Dominance / Striate Cortex / Vision / Cytochrome Oxidase Blobs)," *Proc. Natl. Acad. Sci. USA*, Dec. 1991, 88:11559–63. (Exhibit 7).

Hatsopoulos, Nicholas G. et al., "Information About Movement Direction Obtained From Synchronous Activity of Motor Cortical Neurons," *Proc. Natl. Acad. Sci. USA*, Dec. 1998, 95:15706–11. (Exhibit 8).

Johnson, Paul B. et al., "Cortical Networks for Visual Reaching: Physiological and Anatomical Organization of Frontal and Parietal Lobe Arm Regions," *Cerebral Cortex*, Mar./Apr. 1996. 6:102–19. (Exhibit 9).

Judge, Stuart J. et al., "Implantation of Magnetic Search Coils for Measurements of Eye Position: An Improved Method," *Vision Research*, 1980, 20(6):535–8. (Exhibit 10).

Lukashin, Alexander V. et al., "A Simulated Actuator Driven by Motor Cortical Signals," *NeuroReport*, Nov. 1996, 7(15–17):2597–601. (Exhibit 11).

Lynch, James C. et al., "The Functional Organization of Posterior Parietal Association Cortex," *The Behavioral and Brain Sciences*, Dec. 1980, 3(4):485–534, (Exhibit 12).

* cited by examiner

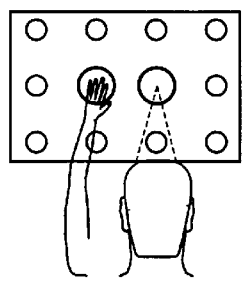
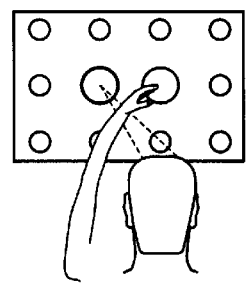
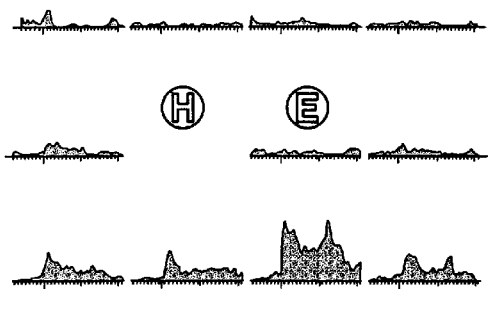
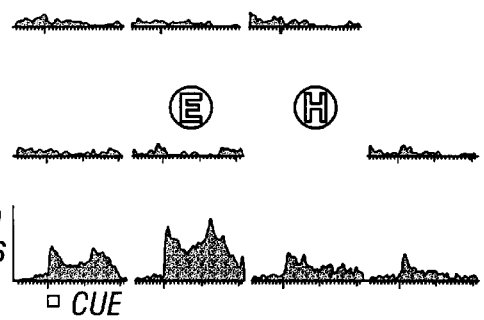
FIG. 2A
FIG. 2C
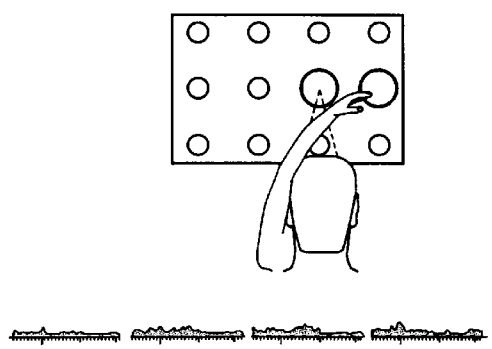
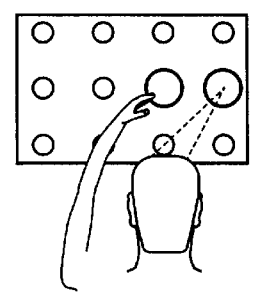
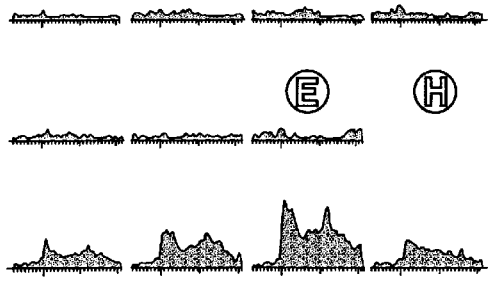
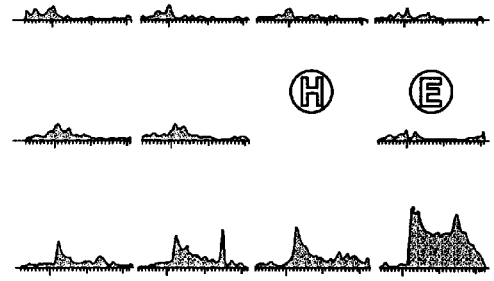
FIG. 2B
FIG. 2D

PROCESSED NEURAL SIGNALS AND METHODS FOR GENERATING AND USING THEM

CROSS-REFERENCE TO RELATED APPLICATIONS

This application is a continuation application of and claims priority to U.S. application Ser. No. 09/369,953, filed on Aug. 6, 1999, now U.S. Pat. No. 6,609,017 which claims the benefit of the filing dates of U.S. Ser. No. 60/095,833, filed Aug. 7, 1998 and U.S. Ser. No. 60/099,222, filed Sep. 4, 1998, the contents of which are incorporated by reference into the present application.

This invention was made with Government support under Grant No. N00014-94-1-0412 awarded by the Office of Navel Research, and with support through the Engineering research Center (ERC) at Caltech, and NSF EEC-9402726 which is a National Science Foundation Center, and NEI EY-05522 awarded by the National Eye Institute which is part of the National Institutes of Health. The Government has certain rights in this invention.

Throughout this application, various publications are referenced within parentheses. The disclosures of these publications are hereby incorporated by reference herein in their entireties.

FIELD OF INVENTION

The present invention relates to processed neural signals that encode a reach plan from a subject for use, for example, to instruct a natural limb or a reach device to carry out the reach plan.

BACKGROUND

Present day limb prosthetics are manually operated, for example by converting electrical signals from a muscle contraction into a mechanical signal to move a limb. This provides only crude control to patients having some remaining limb musculature; thus, it cannot be used by quadriplegics. Recent efforts have been directed to prosthetic limbs that can be controlled directly by a subject's brain. It has been previously determined that the posterior parietal cortex (PPC) plays a role in motor planning, and that planned eye and arm movements are anatomically segregated in the PPC (L H Snyder, et al 1997 Nature 386: 167–170). The steps involved in the act of reaching by a limb (e.g., an arm) of a subject, comprise a reach that includes the steps of: 1) identifying the reach target; 2) planning the reach and also deciding to reach; 3) and executing the reach for the reach target. A planned reach (or reach plan) includes the second step.

The neural events associated with a visually guided reach act begin with an image of the intended reach target on the subject's retinas and end with neural impulses to the muscles of the subject's arm involved in executing the reach. Information about the spatial location of the reach target is initially represented in an eye-centered reference frame that the brain transforms into a limb-centered frame, in order to specify an appropriate reach command.

Information about the reach target location is encoded in visual cortical areas relative to an eye-centered reference frame. In order to execute the arm reach, this spatial information is passed through the PPC and then on to the motor cortex in the frontal lobe which receives this information of the reach target location relative to a limb-centered reference frame. In the brain, the PPC resides between the visual areas that encode spatial information and motor cortical areas that encode movement of a limb. Therefore, the PPC is anatomically positioned to play a role in transforming sensory signals into motor plans, such as a reach act.

The PPC contains several subdivisions, including the lateral intraparietal region (LIP) and the parietal reach region (PRR). The PPC contains neurons that encode an intended movement of a specific part of the body in a specific direction. In particular, a population of neurons within the parietal reach region (PRR) encode the reach plan (L H Snyder, et al 1997 Nature 386: 167–170). The role of the LIP and PRR in motor planning, such as planned saccades and planned reaches, has been previously determined by monitoring the activity of neurons in these regions in Rhesus monkeys, while the monkeys performed interleaved delayed saccade and delayed reach trials (L H Snyder, et al 1997 Nature 386: 167–170). The planned-saccades and planned-reaches are encoded separately by the LIP and the PRR, respectively. Many neurons within LIP area exhibited more neural activity when the monkey planned a saccade, while neurons within PRR exhibited more activity during a planned reach (L H Snyder, et al 1997 Nature 386: 167–170). Furthermore, the activity of the neurons within the PRR is also modulated by the current eye position and the initial hand position of the subject, or the so-called gain field effect (D. Zipser and R A Andersen 1988 Nature 331: 679–684).

Researchers have proposed that each subdivision within the brain encodes its respective movement in the coordinate frame appropriate for making the movement (Colby, Neuron 20: 15 (1998); Rizzolatti et al, Attention and Performance, Umilta and Moskovitch, Eds. (MIT Press, Cambridge, Mass. 1994), vol. 15, pp 231–265). This proposal predicts that the reach target location will be encoded in limb-centered coordinates in the PRR. Surprisingly, the results of the experiments described below show that reach plan-encoding neurons in the PRR encode reach target locations in eye-centered coordinates.

SUMMARY

The present invention provides processed neural signals from reach plan-encoding neurons of a subject, wherein the processed neural signal encodes the reach plan relative to the eye-centered reference frame of the subject. One embodiment of the present invention provides the processed neural signal that encodes a reach target location. Another embodiment provides the processed neural signals that comprise an eye-position gain modulation. Yet another embodiment provides the processed neural signal that encodes an impending reach plan.

The present invention also provides methods for generating the processed neural signal by: acquiring the signal from an activated reach plan-encoding neuron or from a population of activated reach plan-encoding neurons; and processing the acquired neural signal or signals. One embodiment of the methods of the present invention comprises acquiring the signal from an activated reach plan-encoding neuron by detecting the neural signal with a single sensor. A preferred embodiment comprises detecting the neural signal with a multi-sensor array. One embodiment of the methods of the present invention comprises processing the signal from an activated reach plan-encoding neuron. The methods of the present invention further comprise translating the processed neural signal into a control signal that directs a desired action by the subject, wherein the desired action includes movement of: a natural limb; prosthetic limb; or computer screen pointing device.

BRIEF DESCRIPTION OF THE DRAWINGS

FIG. 2: A depiction of a subject engaged in four different reach and fixation tasks involved in the coordinate frame task, and spike density histograms showing the activity of a reach plan-encoding neuron in response to the different reach and fixation tasks (FIG. 1A, B, C and D), as described in Example 1, infra.

DETAILED DESCRIPTION

Definitions

Figure 1:
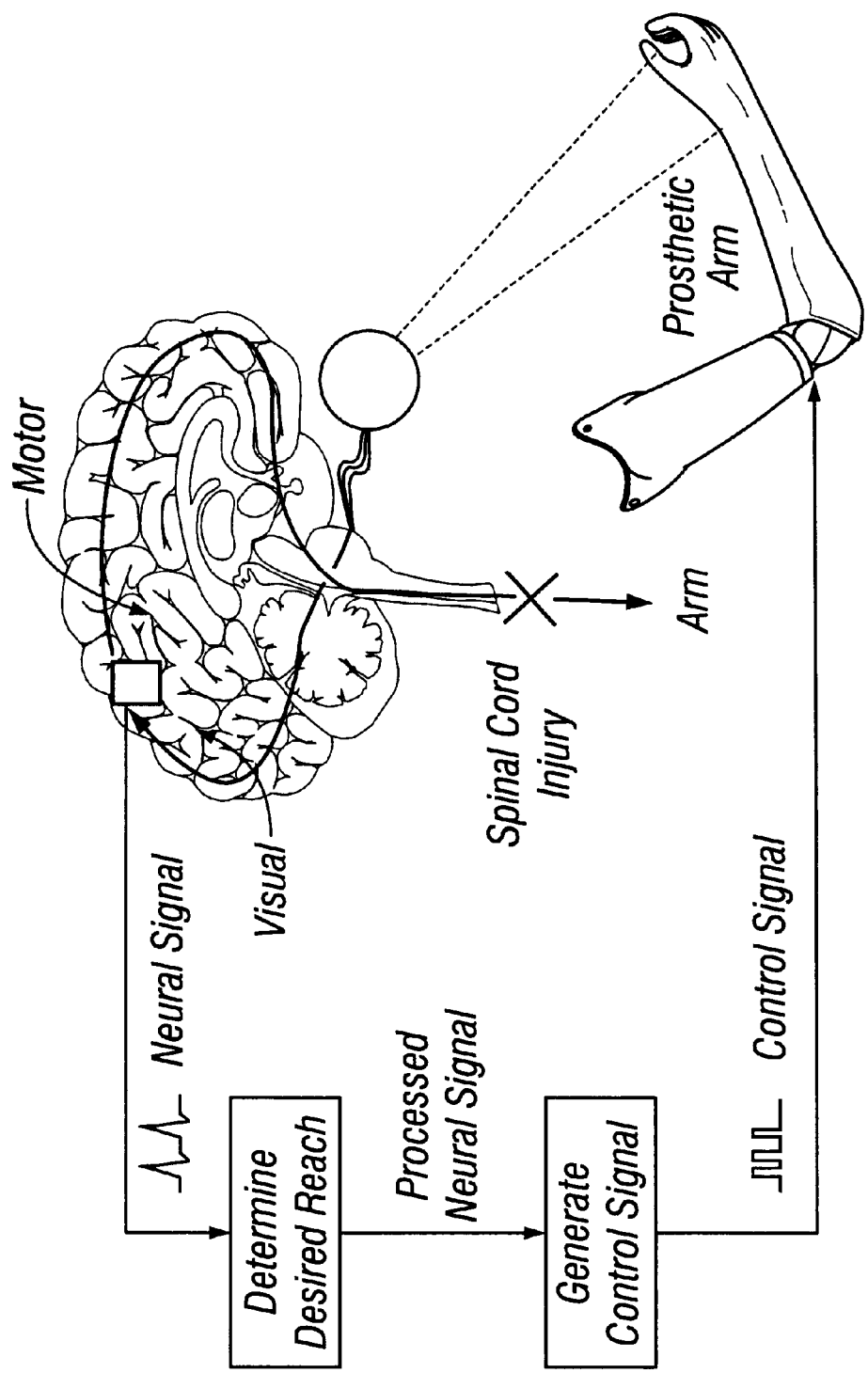
FIG. 1: A schematic representation for a use of a processed neural signal from a reach plan-encoding neuron of a subject in which the neural signals are rerouted to by-pass the non-functional spinal cord.

As used in this application, the following words or phrases have the meanings specified.

The terms "neural activity", "neural signals", and "neural response" used herein are defined to mean a deviation from the background or spontaneous activity generated by a neuron, wherein the background activity occurs while the subject is not planning limb movements. The neural activity may be detected in the form of: chemical concentration, electric field/currents, magnetic fields, and/or changes in blood flow.

The term "processed neural signal" used herein is defined to mean a representation of a neural signal acquired from a reach plan encoding neuron of a subject (e.g., a mammal such as a primate). The processed neural signal is generated by: acquiring a neural signal from an activated reach plan-encoding neuron of a subject; and processing the acquired neural signal so that the final processed neural signal is organized to represent the subject's reach plan relative to the eye-centered reference frame of the subject. The reach plan comprises the selected reach target and the reach target location. The processed neural signal encodes the impending reach plan. The processed neural signal comprises an eye-position gain modulation. The processed neural signal can be represented in the form of: chemical concentration, electric field/currents, magnetic fields, and/or changes in blood flow. It is understood that this definition also encompasses processed neural signals that are generated from a population of reach-plan-encoding neurons of the subject.

The acquiring step comprises detecting the neural activity, using a sensor that detects both the steady state neural activity and the change over steady state activity. The neural activity may be detected in the form of: chemical concentration, electric field/currents, magnetic fields, and/or changes in blood flow. The processing steps comprise signal processing steps that will organize the acquired neural signal to represent the reach plan in the eye-centered reference frame of the subject.

The processing steps include: 1) isolating the activity of individual neurons or a population of neurons from the acquired neural signals; 2) characterizing the isolated signal to determine if it encodes a reach plan, to determine how it responds to reach plans to numerous reach target locations (e.g., determine the tuning curves and preferred location), to determine the receptive fields in eye-centered coordinates, and to determine the eye-position gain modulation; and 3) selecting those characterized neural signals that encode a reach plan, such that the final processed neural signal is organized to represent the target location of the reach plan in an eye-centered reference frame.

The term "saccade" used herein is defined to mean a rapid movement of the eye in its orbit, and no movement of the head of the subject.

The term "reach" used herein is defined to mean a movement of the limb of a subject or a computer screen pointing device, to a desired target location. The limb may be a natural arm or leg, or a prosthetic device that may be attached or not attached to the body. The subject may move any part of the limb to the desired target location. For example, the subject may move a part of the arm, such as the finger, hand, forearm, elbow, or shoulder. The subject may move a part of the leg such as the toes, foot, ankle, heel, knee, or thigh. Alternatively, the reach may comprise moving a computer screen pointing device to any desired location on the computer screen.

The term "reach plan-encoding neuron" used herein is defined to mean a neuron, in a subject (e.g., a mammal such as a primate), that generates a change in signaling activity in response to a planned reach by the subject, wherein the signal encodes information about the reach target location of the planned reach relative to the eye-centered reference frame of the subject. The magnitude of the response by a reach plan-encoding neuron may be influenced by the eye position of the subject; this is known as the eye-position gain modulation.

The term "reach target" or "reach plan target" used herein is defined to mean a target to which a subject intends to reach. The target may correspond to a selected visualized target (e.g., an object), a location in space (e.g., no visualized object), or a remembered target (e.g., no currently visualized object). The subject may intend to reach to the target by moving a limb (e.g., any part of the subject's arm or leg), a prosthetic device which may or may not be attached to the subject, a separate computer screen pointing device, or other device.

The terms "target location" or "reach target location" used herein are defined to mean the spatial location of the selected reach target to which a subject intends to reach. The target location encoded by a reach plan-encoding neuron can be processed to express the target location in coordinates relative to different spatial reference frames relative to the subject, such as: eye-, head-, limb-, body- or world-centered reference frames (e.g., a reference frame not relative to the subject).

The terms "reach plan" and "planned reach" used herein are defined to mean the following. A reach act comprises the steps of: first, perceiving the environment; second, selecting the reach target, and deciding to reach and planning the reach for the reach target at a particular location (e.g., the target location); third, executing the reach for the reach target. The reach plan comprises the second step described herein. Thus, a "reach plan" or "planned reach" comprises the step of: the decision and intention by the subject to initiate a reach for the selected reach target. The reach plan-encoding neuron encodes information about the reach plan relative to the eye-centered reference frame of a subject, comprising the reach target location.

The terms "fixation point" and "point of fixation" and "point of visual fixation" and "fixation position" used herein are defined to mean a point in space at which a subject's gaze is directed, wherein the gaze is understood to mean the angle of the subject's eye within the subject's eye orbit.

The term "eye-centered reference frame" used herein is defined to mean a spatial reference frame anchored or centered relative to a point of visual fixation of a subject. The eye-centered reference frame shifts along with the movement of the subject's eye.

The terms "receptive field", "responsive field", or "motor field" used herein are defined to mean the following. Each reach plan-encoding neuron is responsive (e.g., generates a signal) when the subject plans a reach to a reach target that resides in a region of visual space called the receptive field. A reach plan-encoding neuron exhibits maximum signaling activity when the planned reach to a target location is centered on the neuron's particular "preferred location", which is taken to be the center of the receptive field. The neural activity decreases as the target location of the planned reach deviates from the center of the receptive field. The intensity of the neural response may be expressed as a function of the planned reach distance away from the preferred location. In general, neural response is a function of the target location with respect to the eye and any functional form will provide useful information. The position of the receptive field of each neuron is fixed relative to the fixation point of a subject, and the spatial location of the receptive field shifts along with the shift in the subject's fixation point. That is, as the subject shifts his/her fixation point, the spatial location of the receptive field shifts in the world, but the location does not shift with respect to the eye.

The term "preferred location" as used herein is defined to mean the target location, to which the subject plans to reach, that generates the maximum neural activity. Each reach plan-encoding neuron has a particular "preferred location", which is taken to be the center of the receptive field.

The term "tuning curve" as used herein is defined to mean a function that describes the profile of a receptive field of a reach plan-encoding neuron of a subject. Each neuron's receptive field is mapped or characterized to determine both the center of the receptive field as well as the functional form, or shape, of the receptive field. The shape of the receptive field of a particular neuron can be described as a "tuning curve" that is unique for each neuron. The tuning curve expresses the intensity of the neuron's activity, as a function of the distance between the neuron's preferred location and the planned reach target location (e.g., the tuning curve may be expressed as a Gaussian function or more complex, nonspatially-symmetric, function).

The term "impending reach plan" used herein is defined to mean the next, imminent reach intended to be immediately performed by the subject. A reach plan-encoding neuron encodes the target location of the impending reach plan. These neurons do not hold in memory a representation of subsequent reach plans. The impending reach plan exists, and is encoded by the reach plan-encoding neuron (e.g., for a limited time), even if that reach is never executed.

The terms "acquiring a neural signal" and "an acquired neural signal" used herein are defined to mean detecting the unprocessed neural signal directly from a reach plan-encoding neuron, using a sensor that detects the neural activity. The neural activity may be detected in the form of: chemical concentration, electric field/currents, magnetic fields, and/or changes in blood flow.

The terms "isolating a neural signal" and "an isolated neural signal" used herein are defined to mean a neural signal that has been acquired from a subject, and then processed to determine how many activated neurons were detected by the sensor in order to generate isolated neural signals that represent activity from individual neurons or a population of neurons (e.g., also known in the art as local field potential).

The term "characterizing a neural signal" used herein is defined to mean determining the behavior of a neuron (or a population of neurons) that responds to separately planned reaches to different locations in space. The neuron is examined to determine if it encodes a reach plan, to determine how it responds to reach plans to numerous reach target locations (e.g., determine the tuning curves and preferred location), to determine if the receptive fields are in eye-centered coordinates, and to determine the eye-position gain modulation.

The terms "selecting a neural signal" or "a selected neural signal" used herein are defined to mean choosing a neural signal that encodes a reach plan comprising a target location relative to the eye-centered reference frame of a subject, wherein the correlation of the target location with the eye-centered reference frame is substantial, but need not be 100% (e.g., about 50% to about 100%; see FIG. 3).

The term "control signal" used herein is defined to mean the processed neural signal described above that has been further processed by translating the target location into an instruction (e.g., an electronically coded instruction) that directs a desired action by the subject, such as reaching to the target location. The translation step comprises several steps, including: 1) Transforming the target location of the reach plan, that is encoded by a reach plan-encoding neuron relative to the eye-centered reference frame of a subject, into a target location relative to an appropriate reference frame. The appropriate reference frame may be expressed in coordinates relative to the head-, limb-, body- or world-centered reference frames of the subject (e.g., a reference frame not relative to the subject); 2) Converting the transformed target location into an instruction that directs a desired action by a subject (defined below). The instruction interfaces with the subject's natural limb or a prosthetic device (e.g., an electronic device) to permit the subject to perform a planned reach.

The term "direct a desired action by a subject" used herein is defined to mean a reach, by a subject, of a natural limb or a device to the target location of the impending reach plan. The control signal described above instructs the subject's natural arm or the device to reach to the intended target location. The subject may intend to reach with the natural limb (e.g., the subject intends to move any part of the arm or leg), a prosthetic limb that may be attached or not attached to the subject, or a computer screen pointing device that is not attached to the subject.

The terms "eye-gain modulation", "eye-position gain fields", "gain field", or "gain modulation" used herein are defined to mean an amplification or attenuation of the reach plan-encoding neuron's response to a reach plan. The amplification or attenuation is a function of the eye position in the eye orbit of the subject. This concept extends to gaze modulation, where the angle of the eye in the orbit plus the angle of the head on the body (proprioceptive and efference cues), or in the world (vestibular cues), may modulate the neural activity. The preferred location and the form of the tuning curve of this neuron remain largely unchanged, but the entire tuning curve is amplified or attenuated by the gain field. Each reach plan-encoding neuron has its own unique gain modulation, and the influence of the eye position on the activity of the neuron may be weak or strong. The signal from a reach plan-encoding neuron having a strong eye-position gain field encodes information about both the target location of a reach plan and the eye position of the subject.

In order that the invention herein described may be more fully understood, the following description is set forth.

Processed Neural Signals

The present invention includes the discovery that a reach plan-encoding neuron, such as a neuron found in the PRR, generates a change in signaling activity in response to an impending planned reach by the subject. The reach plan is encoded relative to the eye-centered reference frame of a subject. A reach plan-encoding neuron encodes at least some of the information about the target location relative to the eye-centered reference frame of a subject, wherein the correlation of the target location with the eye-centered reference frame is substantial. The activity of these neurons changes when the subject plans a reach for a target location, and the activity returns to the background or spontaneous activity level after the subject initiates the reach. The impending reach plan exists, and is encoded by the reach plan-encoding neuron, even if that reach is never executed. The amplitude of the response by a reach plan-encoding neuron may be influenced by the eye position of the subject. This has been previously described as an eye-position gain field (Zipser and Andersen 1988 Nature 331: 679–684), and the influence may be weak (or negligible) or strong.

The present invention provides a processed neural signal that encodes a reach plan, wherein the reach plan is encoded relative to the eye-centered reference frame of the subject. The reach plan comprises the selected reach target and the reach target location. The processed neural signal encodes the impending reach plan. The processed neural signal comprises an eye-position gain modulation.

A group of reach plan-encoding neurons collectively encode the target location of an impending reach plan. In a normal subject, the target location is interpreted by motor-related cortical areas, where the detailed commands for motor action are created. After further refinement by brain stem and spinal cord neurons, control signals activate muscle groups in the arm. This signal pathway is destroyed by limb injury, upper spinal cord damage, or stroke. It is a goal of the present invention to bypass this signal pathway and to use the processed neural signal to directly instruct a natural limb or a reach device (e.g., a limb prosthetic or a computer screen pointing device) to carry out the reach plan.

The processed neural signals of the present invention are useful for assisting a subject, such as a human subject, that is not capable of limb movement due to an upper spinal cord injury, a stroke within the motor cortex, neuro-degenerative disease or limb amputation. The processed neural signals may form the basis for neural prosthetic devices in which the subject's own neural signals interface with electronic devices that permit the subject to perform a planned reach. The normal neural signal pathway may be rerouted around the afflicted area and used to directly instruct an arm or a reaching device to perform the planned reach (see FIG. 1). The processed neural signal is generated by acquiring, isolating, characterizing, and selecting the reach plan-encoding neural signals from activated reach plan-encoding neurons of a subject.

The usefulness of the processed neural signal results from the inclusion of reach plan-encoding signals that encode planned reaches relative to the eye-centered coordinates of a subject, where the reach plan-encoding signals can be processed and decoded to reconstruct the target location of the reach plan relative to an appropriate coordinate frame (e.g., such as relative to the subject's head or limb). For example, the processed neural signal may be translated into a control signal that instructs a natural limb or a device to perform the planned reach.

In particular, the subject may perform the planned reach by moving any part of a natural limb or prosthetic limb to the desired target location. The prosthetic limb may be attached or not attached to the subject; for example, the prosthetic limb may be attached to the subject's limb stump or to the subject's wheelchair. Alternatively, the subject may perform the desired reach by moving a computer screen pointing device to the desired target location on the computer screen. Additionally, the processed neural signal is useful for determining how the brain encodes the spatial coordinates of a reach target, and for analyzing the mechanism of mammalian brain coordinate transformation.

A reach plan-encoding neuron encodes a relatively straight-forward representation of a reach plan compared to reaches encoded by other regions, such as the motor cortex. A reach plan-encoding neuron encodes the target location of an impending reach plan relative to the eye-centered coordinates of a subject. In contrast, the motor cortex more likely encodes multiple steps of the reach act including the steps of a reach plan and executing the reach (A B Schwartz 1993 J. Neurophysiology 70: 28–36; Lukashin et al 1996 NeuroReport 7: 2597–2601). Furthermore, the motor cortex encodes the target location relative to a more complex set of coordinate frames such as a limb. The motor cortex also encodes the muscle forces to move the arm to the reach destination (Lukashin et al 1996 NeuroReport 7: 2597–2601). Thus, it is advantageous to use processed neural signals from reach plan-encoding neurons to represent the destination of a planned reach rather than from the motor cortex. Another advantage is that a reach plan-encoding neuron most likely maintains the reach plan information relative to an eye-centered reference frame even after the subject experiences a limb injury, amputation, or upper spinal cord damage. This is because the reach plan-encoding neurons are less involved with detailed muscle control and receive less proprioceptive information from the periphery. In contrast, neurons within the motor cortex would likely experience substantial reorganization after injury that may render them ill-suited to planning limb movements.

Methods for Generating Processed Neural Signals

The present invention additionally provides methods for generating processed neural signals of the invention. In one embodiment, the methods comprises the steps of: 1) acquiring a signal from the activity of the reach plan-encoding neuron of the subject, wherein the acquired neural signal is in a form that can be processed; and 2) processing the neural signal to represent the target location of the reach plan relative to the eye-centered reference frame of a subject, wherein the acquired neural signal is processed by isolating, characterizing, and selecting to interpret the information included in the neural signal.

A neural signal originates from the brain of a subject, for example a mammal such as a primate, while the subject is planning a reach. Rhesus monkeys are an appropriate animal model for analyzing the reach plan-encoding neurons and for applying this discovery to use in humans, because the posterior parietal cortex (PPC) is similar in Rhesus monkeys and humans (Andersen 1987 in: Handbook of Physiology: The Nervous System V 483–518, eds: Mountcastle, Plum and Geiger; J C Lynch 1980 Behav. Brain Sci. 3: 484–534). However, the methods described herein can generate processed neural signals in other subjects, including but not limited to, a human, dog, or cat.

The neural signals of the present invention originate from neurons in a region of the brain that has been previously identified as encoding planned movements, such as saccades or reaches (L H Snyder, et al 1997 Nature 386: 167–170). The region of the brain is preferably the PPC region and most preferably the parietal reach region (PRR) region. In Rhesus monkeys, the PRR has been previously located on the medial bank of the intraparietal sulcus and just anterior to the parieto-occipital sulcus (POS) (L H Snyder, et al 1997 Nature 386: 167–170). In particular, the PRR is positioned about 5 mm posterior and 5 mm medial with respect to the lateral intra-parietal area (LIP), which is approximately 5 mm posterior and 7 mm lateral in stereotaxic coordinates.

In the experiments described herein, the neurophysiological recordings were made from a region that presumably overlaps with areas V6A (C. Galletti, et al 1997 Eur. J. Neurosci. 9: 410) and MIP (PB Johnson et al 1996 Cereb. Cortex 6: 1047; C L Colby and J. -R. Duhamel, 1991 Neurophsychologia 29: 517). In humans, the PRR has been previously estimated to be located posterior to LIP in the superior parietal lobule.

An activated reach plan-encoding neuron generates a signal in response to a reach plan. It is well known in the art that this neural signal may be detected in the form of: chemical concentration, electrical field/current, magnetic fields and/or blood flow. For example electro-physiological techniques detect electrical pulses, called action potentials or "spikes". In this case, the frequency of action potentials (also known in the art as firing rate, spikes per second or spike density) is taken to be a measure of the neural activity, or response. In another example the intrinsic signal related to blood flow may be detected with optical imaging (A. Grinvald, et al. 1991 PNAS 88: 11559–11563). Additionally, other response measurements, such as the precise time of spikes or the relationship between the spike times of two or more neurons are also valid and used by those skilled in the art.

It is advantageous that the activity of a population of reach plan-encoding neurons (e.g., two or more) be detected in order to determine the reach target location more precisely. Therefore, it is understood that the present invention encompasses a plurality of processed neural signals acquired from a population of reach-plan-encoding neurons in order to determine the target location more precisely.

A neural signal can be acquired from an awake subject, e.g., Rhesus monkeys, by standard electrophysiology techniques (V B Mountcastle, et al 1975 J. Neurophysiol. 38: 871–908) using sensors that detect electrical activity of an activated neuron. The neural activity is detected while the subject is planning a reach or not planning a reach.

The sensor output signal is conditioned and transmitted for input to the acquisition system. Signal conditioning, if required, may include signal amplification and/or filtering, as appropriate. Signal conditioning requirements depend on the-type of sensor used and on the input specifications of the acquisition system. Signal conditioning is a standard step in the art of data acquisition systems.

The acquisition system measures the sensor signal. In the described experiments, the amplified voltage signal from the sensor is sampled and digitized into discrete voltage values by an analog-to-digital converter.

Typically, a single sensor (e.g., a metal electrode) is introduced into the PRR of the subject's brain, and the sensor detects between about one to four neurons. Therefore, the activity of more than one neuron may be acquired using a single sensor. The acquired signals are then processed by a technique known in the art as spike sorting, in order to generate isolated neural signals that represent activity from individual neurons or from a population of neurons (M Sahani, et al. 1998 Extracellular Recording From Multiple Neighboring Cells: A Maximum-likelihood Solution to the Spike-separation Problem. In: Computational Neuroscience: Trends in Research Ed. J M Bower. Plenum Press, New York; M Sahani et al. 1998 On the Separation of Signals From Neighboring Cells in Tetrode Recordings. In: Advances in Neural Information Processing Systems 10 Eds. M I Jordan, M J Kearns, and S A Solla. MIT Press. Cambridge Mass.). However, the activity of a population of neurons may have an aggregate tuning curve and may, therefore, also be useful. The acquired signals are sorted since each neuron has a unique receptive field. One embodiment of the present invention comprises the steps of processing the acquired neural signal, including the step of isolating the neural signal that encodes the activity of a single neuron or a population of neurons.

To acquire signals from different neurons in one region of the brain, the single electrode sensor is repositioned numerous times and the activity monitored with each introduction. One embodiment of the present invention comprises the step of detecting the neural signals of a population of neurons using a single electrode sensor that is reintroduced into different sub-regions within the brain of a subject, and the activity is monitored with each introduction. A preferred embodiment comprises the step of introducing a plurality of single electrode sensors into the same region of the brain, thereby permitting simultaneous detection of signals from different neurons within a region of the brain.

The method of detecting neural activity using a plurality of single electrode sensors is reliable, but it does not permit detection of neural activity from exactly the same neurons once the sensors have been repositioned. However, the development of commercially-available multi-sensor arrays (available from Bionic Technologies, covered by U.S. Pat. No. 5,215,088; Nicolelis 1999 Methods for Neuronal Ensemble Recordings, CRC Press, Boca Raton, Fla.; Hatsopoulos et al 1998 PNAS 95: 15706–15711) makes it possible to simultaneously introduce numerous electrodes (eg: between about 20 to 200) and to monitor the same neurons for an extended period of time without repositioning the sensor.

The detection of signals from specific neurons that are located at different depths within the brain is determined by the length of the electrodes contained on the single sensor or the multi-sensor array, as well as the placement of the sensors. In order to detect signals from neurons located at various depths within the cortex, the single electrode sensor may be introduced at the desired depth in the cortex. The multi-sensor array may contain electrodes that are all the same length in order to detect signals from neurons located at a particular depth. Alternatively, the multi-electrode sensor may contain electrodes each having different lengths in order to simultaneously detect signals from neurons located at varying depths. For example, the length of the electrodes may be graded from short to long. The multi-sensor length profile may be designed so as to sample the optimal distribution of neurons in order to optimize the target location estimation accuracy. Additionally, the multi-sensor array may be constructed with a desired number of electrodes. For example, the array may contain between about 20 to 200 electrodes. One embodiment of the present invention comprises the step of detecting the neural signals using a multi-sensor array having electrodes between about 0.5 to 2.0 mm in length. Another embodiment comprises detecting neural signals using a multi-sensor array having between about 20 to 200 electrodes.

In one embodiment, the method used to introduce a single electrode sensor into the PRR of a subject, e.g., a Rhesus monkey wherein the PRR is located on a sulcal bank, involved advancing the electrodes along the sulcal wall until the electrode tip rests in the cortical area. The electrode tip was stereotaxically positioned without additional surgery. This method may also be practiced by advancing several single electrodes to the same area of the brain; however it is not possible to deliver more than (perhaps) ten single electrodes to the cortical area, because the cortical area presents a small cross-sectional area in a dorsal-ventral view (e.g., top-looking-down).

In another embodiment, the method used to introduce electrode sensors involves surgically implanting a single multi-sensor array directly into the cortical region of the subject. The sulcal wall can be surgically separated and the multi-sensor array implanted into the cortical region. This method is advantageous because it allows precise placement of the sensor in the desired region. Additionally, more than one array may be implanted.

The behavior of each monitored reach plan-encoding neuron must be analyzed to determine if the gain modulation is weak or strong. In order to characterize the effect of eye-gain modulation, the eye position is monitored or tracked while the subject plans a reach. One method to monitor the subject's eye position uses scleral eye coils that are surgically implanted in the subject's eyes (Judge, S. J. et al 1980 Vision Res.20: 535–538). Another method of tracking the subject's eye position is to monitor a population of eye-position coding neurons, such as neurons within LIP. Alternatively, a non-invasive technique involves infra-red optical eye trackers (e.g., available from ISCAN, Corp., Mass.)

The Reach and Saccade Tasks

The neural signals are acquired from a population of neurons that are characterized as being reach plan-encoding neurons. The neural signals are acquired from a subject, such as Rhesus monkeys, while the subject performs specific reach and saccade tasks thereby permitting correlation of the neural activity and the tasks. The subjects are trained to reach or saccade to the remembered locations of flashed visual targets. The conditions of the reach and saccade tasks are known and commonly used in the art of electro-neurophysiology. Furthermore, the interleaved trials have been described previously (L H Snyder et al (1997) Nature 386: 167–170).

The Gain Modulation

A population of selected signals that represent reach plan-encoding neurons collectively encodes the target location of a reach plan. In order to decode the target location, it is essential to generate a database that includes characterized parameters of the selected neurons. The database may include characterized parameters of: the receptive fields in eye-centered coordinates and the eye-position gain modulation. The eye position gain field may be used in order to decode the target location in head-centered coordinates (Zipser and R A Andersen 1988 Nature 331: 679–684). It has been previously shown that each reach plan-encoding neuron has its own unique eye position gain field, wherein the influence of the subject's eye position on the activity of the neuron may be weak or strong (Zipser and Andersen 1988 Nature 331: 679–684; Batitsta, et al 1999 Science 285: 257–260). When the influence of the eye position gain field is strong for particular neurons within the population, then the population may encode both the eye-centered target location and the eye position. The strong influence of the eye position gain field provides information for decoding the target location relative to the subject's head.

If the eye position gain field is weak (or negligible), then only the target location, with respect to the eye, can be decoded directly from the neural signals. A separate source of eye position information, from an eye tracking system or from a chronic electrode array monitoring a population of eye-position coding neurons (e.g., area LIP), may be added to the eye-centered position of the reach end-point to arrive at the reach end-point with respect to the head. The position of the head on the body could similarly be included to arrive at the reach end-point with respect to the body.

Coordinate Transformation

If signals from reach plan-encoding neurons are strongly influenced by the eye-position, then the neurons likely encode a distributed representation of the target location with respect to the subject's head. In this case, the measured neuronal activity must first be transformed (e.g., coordinate transformation) into a distributed representation encoding the target location with respect to the head (Zipser and Andersen 1988 Nature 331: 679–684). The eye-centered location can also still be read out from this distributed representation (Pouget and Sejnowski 1995 Adv. Neural Inf. Process. 7: 157–164). This may be done using a neural net solution (D E Rumelhart, et al 1986 in: Parallel Distributed Processing: Explorations in the Microstructure of Cognition Vol. 1 eds: Rumelhart, McClelland, MIT, Cambridge, Mass.). This transformation takes the eye position modulate into account and yields a distributed representation in head-centered coordinates. (Zipser and Andersen 1988 Nature 331: 679–684).

Decoding the Acquired Neural Signal

After determining the influence of the eye position gain field, the information encoded by, reach plan-encoding neurons can be decoded to determine the target location of a planned reach, and to reconstruct the target location of the planned reach.

The algorithms used for decoding the reach end-point (azimuth and elevation) from a distributed representation and for transforming a eye-centered, eye-position gain modulated representation into head-centered representation may follow that of novel and existing reconstruction algorithms (Salinas and Abbott 1994 J. Comput. Neurosci. 1: 89–107; Salinas and Abbot 1995 J. Neurosci. 15: 6461–6474; Lukashin et al 1996 NeuroReport 7: 2597–2601; Zhang et al 1998 J. Neurophysiol. 79: 1017–1044). It is important to note that while temporal synchrony may be found (i.e., correlations in time) among the simultaneously recorded neurons, which may lead to more accurate decoding algorithms, it is assumed that the mean firing rates of the reach plan-encoding neurons are tuned for the location of the desired reach and contain substantial reach target information.

The following examples are presented to illustrate the present invention and to assist one of ordinary skill in making and using the same. The examples are not intended in any way to otherwise limit the scope of the invention.

EXAMPLES

Example 1

The PRR neurons encode the target location relative to an eye-centered reference frame To determine if reach plan-encoding neurons encode a reach plan relative to the subject's limb- or eye-centered reference frame, neurons within the PRR were tested in a coordinate frame experiment (A P Batista, et al July 1999 Science 285: 257–260). The coordinate frame experiment involves modified conditions of a delayed reach task. In two conditions, different reaches were performed to targets at the same visual location. In another two conditions, the same reach was made to targets at different visual locations. This four-condition paradigm permitted independent observation of the effects of manipulating the target location in sensory and motor reference frames on the PRR neurons.

The neuro-physiological recordings were made from the PRR region that presumably overlaps with areas V6A (C. Galletti, et al 1997 Eur. J. Neurosci. 9: 410) and MIP (PB Johnson et al 1996 Cereb. Cortex 6: 1047; CL Colby and J. R. Duhamel, 1991 Neurophsycologia 29: 517).

A vertically oriented, curved array (radius of about 30–40 cm) of touch-sensitive buttons was placed in front of the monkey. The touch screen was a square grid spanning about 54°×36° of the visual field with about 18° push-button spacing. Each button contained a red and green LED.

The position of the illuminated red or green LED was varied. Four different configurations of eye and initial hand positions were used. In two conditions, the red LED instructing visual fixation was at the button located straight ahead, and the green LED instructing the initial button press was 18° or 36° to the left or right of the straight ahead button. In the other two conditions, the green LED was at the straight-ahead button, and the red LED was 18° to the left or right. For each neuron, the four initial configurations were randomly interleaved for five repetitions of reaches to each target. The delay period was either 800 ms, or it was a random duration between 600 and 900 ms. For each neuron, the four initial configurations were interleaved for five repetitions of reaches to each target.

The two conditions of the coordinate frame trial in which reaches were performed from two different locations to targets at the same visual location is shown in FIG. 2, panels A and B. The trial began with the animal fixated on the red center button, and the initial hand position was located at a green button (the initial green button) located either to the left or right of the center red button. A second green button was illuminated briefly, at the position of any unlit button; this is the reach target button. The animal plans a reaching arm movement to the target location but does not immediately perform the reach. Then the initial green button was extinguished, and the animal executed the reach to the remembered target button. When the target button was depressed, the center red LED was extinguished, thereby releasing the fixation command.

The two conditions of the coordinate frame trial in which the same reach was performed to targets at different visual locations is shown in FIG. 2, panels C and D. The trial began with the animal fixated on a red button located either to the left or right of the straight ahead button, and the initial hand position was located on the straight ahead green button (the initial green button). A second green button was illuminated briefly, at the position of any unlit button; this is the reach target button. Again, the animal plans a reaching arm movement to the target location but does not immediately perform the reach. Then the initial green button was extinguished, and the animal executed the reach to the remembered target button. When the target button was depressed, the red button was extinguished, thereby releasing the fixation command.

FIG. 2 shows the results of a reach plan-encoding neuron in the monkey's PRR tested in the four-conditions paradigm. Panels A and B illustrate the effect of varying the initial hand position: the neuron's response is similar in the two conditions, demonstrating that the neuron is largely insensitive to the target location relative to the monkey's limb-centered reference frame. Panels C and D illustrate the effect of changing the initial direction of fixation: the neuron's response changes markedly, demonstrating that the neuron is sensitive to the target location relative to the monkey's eye-centered reference frame. That is, the receptive field of this reach plan-encoding neuron is anchored to the eye, but not to the body (e.g., relative to the subject's head or limb) or world-centered coordinates. In all four cases, The neuron's preferred location is constant relative to the direction of gaze, that is down with respect to the point of fixation. This neuron is selectively activated by planned reaches, and encodes the target location in an eye-centered reference frame.

Example 2

Correlation Analyses

The, results of the neuron shown in FIG. 2 are exemplary of a population of numerous neurons from monkeys tested in this experiment. The data from all neurons tested in the two conditions in which the same reach was performed from different initial limb positions (FIG. 2A and B) and in the two conditions in which the targets were at different visual locations (for example, FIG. 2C and D) was further analyzed using a correlation analysis.

The average firing rate during the delay interval (from 100 ms after cue offset to the "go" signal) was used to compute the correlations. The formula employed was:

To compute the correlation in eye-centered coordinates, xi is the average firing rate for a reach to a given target i from an initial hand position to the left, and yi is a reach to the same target from an initial hand position to the right, with the same fixation position, 'x is the average of the xi, 'y is the average of yi and n is the number of targets that overlapped in the two configurations. To compute the correlation in hand-centered coordinates, xi and yi are the average firing rates for reaches to target i, with the eyes fixating to the left (x) or to the right (y) with the same initial hand position. For most neurons, there were between eight and eleven overlapping locations. If there were fewer than three overlapping locations, the neuron was not included in the correlation analysis.

The results of the correlation analysis is shown in FIG. 3. Each point represents data from one neuron. For each neuron, the correlation between the two tuning curves that have a common eye position (eg: FIG. 2A and B) is plotted on the horizontal axis and the correlation between the two tuning curves that have a common initial hand position (eg: FIG. 2C and D) is plotted on the vertical axis. The diagonal line represents equal correlation in limb-centered and eye-centered reference frames.

Figure 3A:
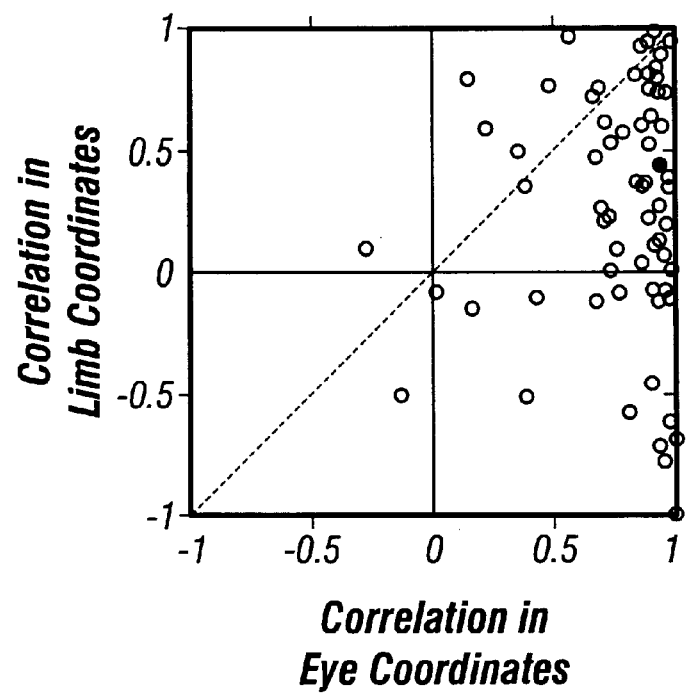
FIG. 3: A): A reference frame analysis of a population of reach plan-encoding neurons tested in a coordinate frame trial, as described in Example 2, infra. B): A representation of the tuning curves collected with the same initial hand position but shifted into the eye-centered alignment, as described in Example 2, infra.

The correlation analysis of 74 neurons are shown in FIG. 3. The symbol "•" in FIG. 3 represents the neuron shown in FIG. 2. The results of the correlation analysis depicted in FIG. 3A shows that 84% of the neurons tested lie below the line of equal correlation; therefore, these neurons show a greater correlation with an eye-centered rather than a limb-centered reference frame. This provides further support for the conclusion that certain neurons within the PRR encode the target location of the planned reach relative to the monkey's eye-centered reference frame.

Figure 3B:
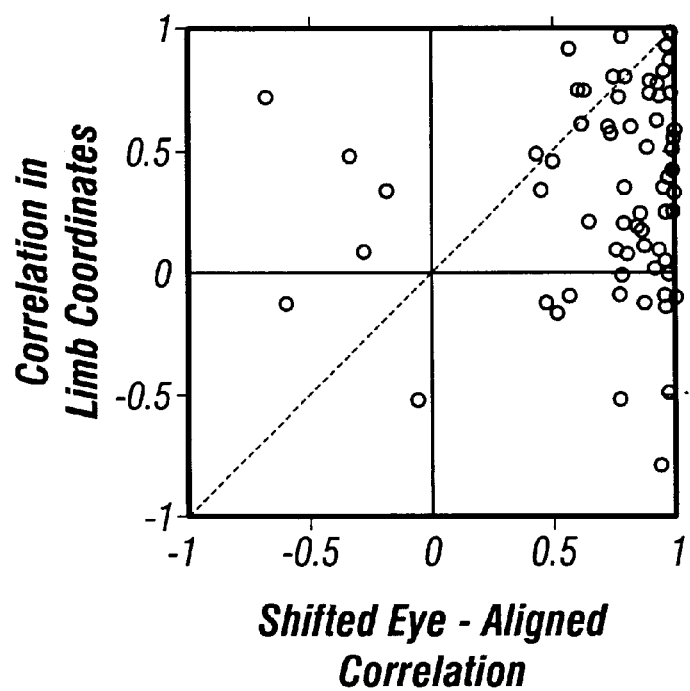

Another method was used to determine if neurons within the PRR encode the target location of a planned reach in an eye- or limb-centered reference frame. The two tuning curves measured with the same initial hand position but with different eye positions were shifted into alignment in eye-centered coordinates. The results of this analysis are shown in FIG. 3B, and demonstrate that 81% of the neurons tested correlated better when the tuning curves were shifted into eye-centered alignment than when they were not shifted.

Thus, two different methods of analyzing the neural recordings from the four-condition paradigm show that most neurons within the PRR encode planned reaches relative-to the monkey's eye-centered reference frame.

Example 3

The Effect of the Gain Modulation

The amplitude of the reach plan-encoding neuron signal is influenced by the subject's eye position, also known in the art as eye-position gain modulation. The gain effects of the current eye position and initial hand position on the peak response of the neurons that were most strongly eye-centered were computed. The interaction between the initial eye and hand position, and the response by the neurons were modeled as a function of eye or hand position multiplied by the response profile of the receptive fields. To compute the average arm position gain, the results of neurons showing activity relative to eye-centered coordinates of 0.9 or greater were used (50% of neurons included in the coordinate frame analysis). 41% of neurons had a correlation of 0.9 or greater and overlapping peaks in retinal coordinates, for the tuning curves with common initial hand position. These neurons were used for the computation of the average eye position gain.

The average computed gain effects for varying the initial hand position changed the peak response by 0.39% per degree, and varying the eye position changed the peak response by 0.78% per degree. This information may be used to compute the reach target location in head-centered or hand-centered reference frames.

Example 4

The Reach Plan-encoding Neuron Encodes the Impending Reach Plan

To determine if reach plan-encoding neurons within the PRR encode memorized target locations of more than one reach target, or if they encode the target location of only the next impending planned reach, the neurons were tested with an intervening reach task.

Typically, the intervening reach task began with the monkey fixating and touching the center button. A first target was presented within a neuron's receptive field, then a second target was presented outside this neuron's receptive field. The monkey was directed to execute sequential reaches to two remembered targets in the reverse order in which the targets were presented. The subject maintained fixation at the center button during the trial.

The intervening reach task began with the monkey fixating and touching the center illuminated button. The first target was presented for 300 ms inside a particular neuron's receptive field. After a delay period of 500 ms, a second target was presented for 300 ms outside of the receptive field. A delay interval of 448 ms ensued before both fixation points were extinguished, signaling a reach to the location of the second target. Once the monkey pushed this button, the green LED at that location and the red LED at the center button turned on, initiating a 500 ms delay epoch. Both LEDs were extinguished again, and the monkey reached to the location where the first cue had been presented. The monkey had to maintain central fixation throughout the trial. Interleaved with trials of this type were trials of the delayed reach task where the first target was presented alone. For these trials, the delay period was lengthened to match the duration from the first target presentation to the first "go" signal of the intervening reach task.

Figure 4:
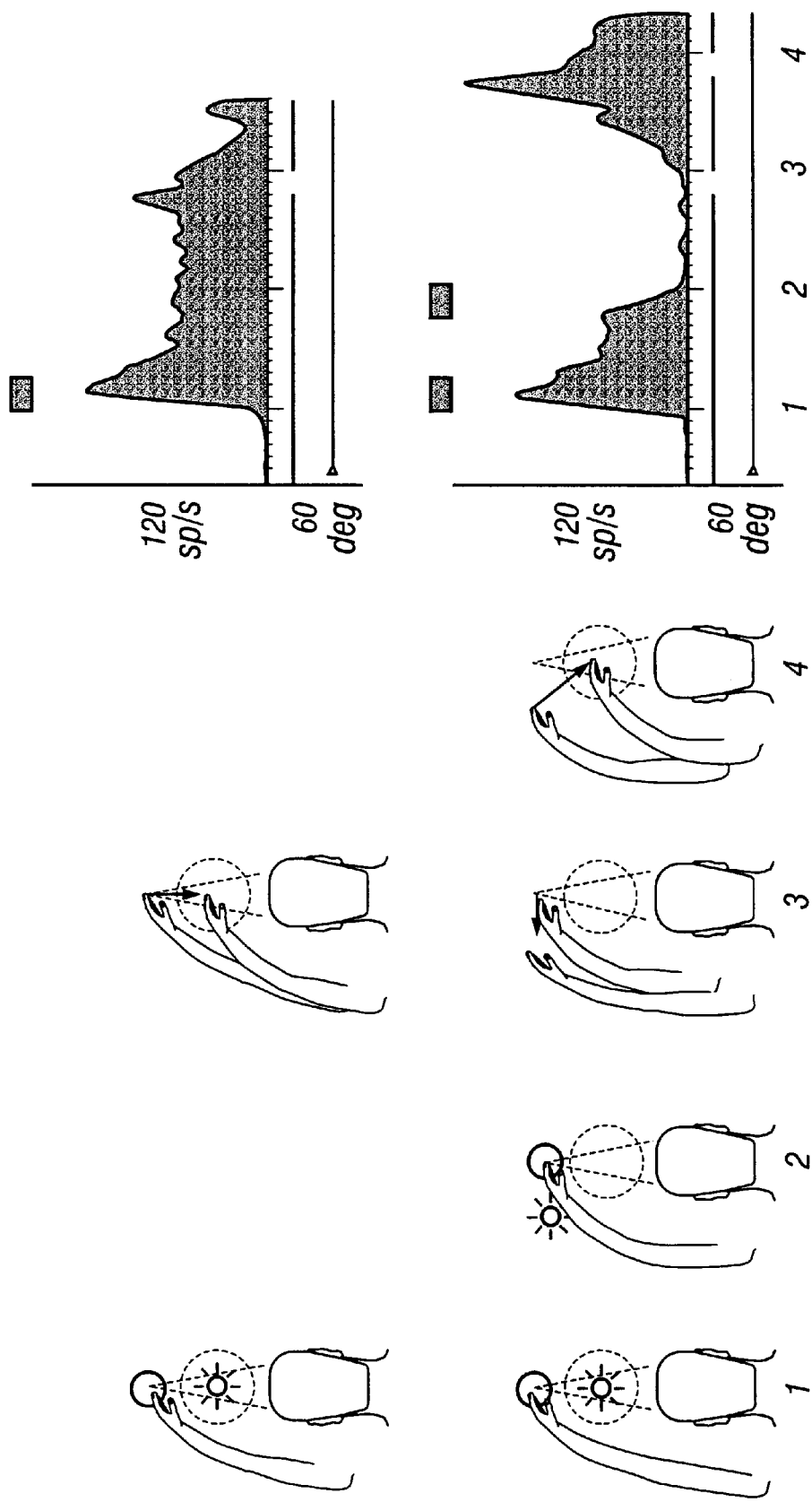
FIG. 4: A schematic representation of the behavior of one reach plan-encoding neuron tested in an intervening reach task. The upper panel shows a subject engaged in a delayed reach task where only one target is presented and the activity of a reach plan-encoding neuron; the lower panel shows a subject engaged in an intervening reach task and the activity of a reach plan-encoding neuron, as described in Example 4, infra. The bars above the spike histograms show the timing of the cues; the second cue is presented only in the intervening reach task. The thick trace below the histograms shows the time courses of button presses. The thin trace below the histograms tracks the subject's eye position during the reach task.

The results of a reach plan-encoding neuron tested with the intervening reach task is shown in FIG. 4. The neuron exhibited sustained activity following presentation of the first target within its receptive field. Then the activity of this neuron decreased when the subject was directed to change its reach plan to the second target located outside of the receptive field. The subject performed a reach to the second target, then reached for the first target. The activity of this neuron again increased after the first reach and when the second impending reach was to a location within the receptive field. These results suggest that reach plan-encoding neurons within the PRR encode the target location of an impending reach plan.

A subset of these neurons were tested in the inverse configuration: the first target was presented outside the receptive field, and the second target was presented within the receptive field. In this trial, the neurons exhibited increased activity when the second reach target was presented within the receptive field, then the neural activity decreased when the subject reached towards the first target. The results of all tasks described in this section support the conclusion that reach plan-encoding neurons within the PRR encode the target location of the impending reach plan.

A neuron was considered to signal only the impending reach if its activity from 100 to 500 ms after the presentation of the first cue was not significantly different (two-tailed Mann-Whitney test p<0.05) between the intervening reach task and the delayed reach task, and its activity from 100 to 448 ms after the second cue in the intervening reach task was significantly lower (one-tailed Mann-Whitney test p<0.05) than its activity during the corresponding time period in the delayed reach task. The results of these experiments provided no evidence that neurons within the PRR encode the first target during the delay following presentation of the second target. Thus, all neurons in this experiment were responsive only for the next movement of a planned sequence of movements.

Example 5

The Reach Plan-encoding Neuron Compensates for a Saccade

To determine if reach plan-encoding neurons update their representation of the remembered target after a saccade, neural signals were acquired from a monkey performing a saccade while planning a reach in an intervening saccade trial. This intervening saccade task is a modification of the coordinate frame task.

Figure 5A:
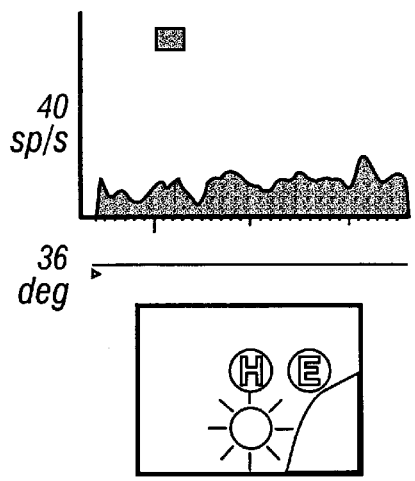
FIG. 5: Spike density histograms showing the activity of a reach plan-encoding neuron in response to reaches, with (see FIG. 3C) and without (see FIGS. 3A, B) an intervening saccade, to the same reach target as described in Example 5, infra. A population analysis of the reach plan-encoding neurons tested in the intervening saccade trial (FIG. 3D), as described in Example 5, infra.
Figure 5B:
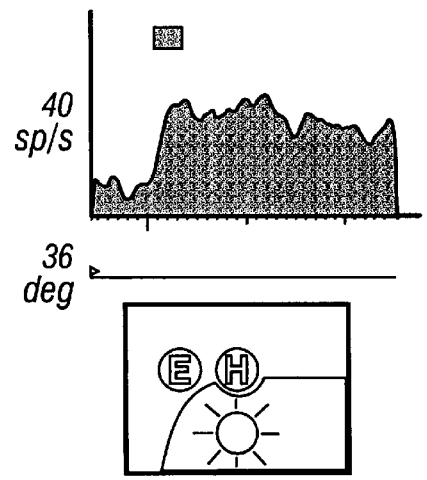
Figure 5C:
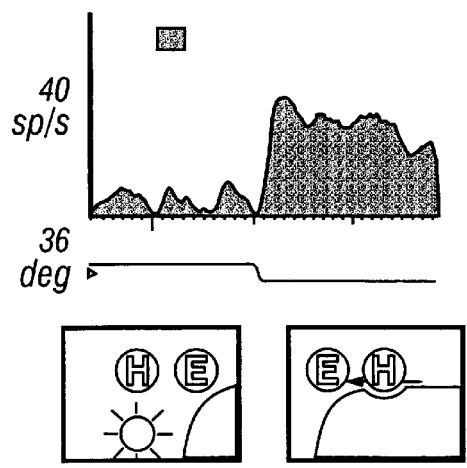

An eye-centered representation of a reach plan may potentially be disrupted if the eyes move before the reach can be executed, particularly if the reach is to a remembered location in the dark. To test whether PRR can compensate for a saccade, monkeys were trained to make a saccade while planning a reach; this is an intervening saccade task. The reach target was presented outside of or on the edge of the response field, and then, after the target was turned off, a saccade was instructed that brought the reach goal into the center of the response field. FIG. 5C shows a neuron tested in this task. Before the monkey makes a saccade, the neuron's response is low, indicating the target is out of the response field (FIG. 5A). After the saccade, the neuron responds at a higher rate, similar to its response when the target actually appears in the response field (FIG. 5B). A neuron was deemed to exhibit compensation for saccades if its response after the saccade was significantly greater (Mann-Whitney test, P<0.05) than its response in the task where the target is presented out of the response field and no saccade is made (as in FIG. 5A).

Figure 5D:
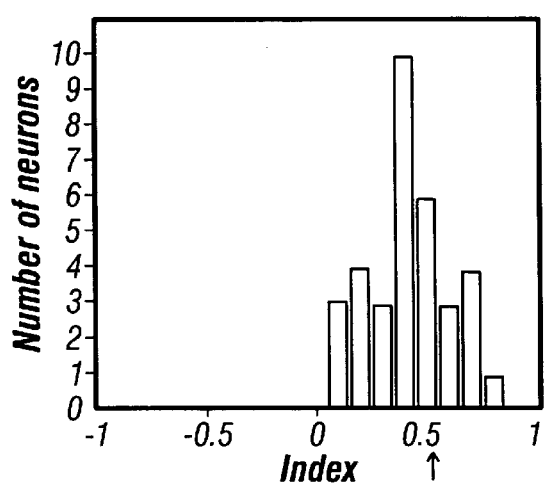

A population analysis of the results of the intervening saccade is shown in FIG. 5D. The arrow in FIG. 5D indicates the index value of this neuron tested in the intervening saccade trial. The reach plan-encoding neurons tested with the intervening saccade trial showed an increase in activity when the saccade brought the remembered target location within a particular neuron's receptive field (FIG. 5D).

In fact, all neurons tested in this experiment showed compensation for saccades (FIG. 5D). Thus, neurons within the PRR compensate for saccades to preserve correct encoding of reach targets in an eye-centered reference frame. This is an important advantage for a prosthesis since it will accurately record planned reach locations in eye coordinates regardless of what the eyes are doing.

A subset of these neurons were also tested in the inverse configuration: the target was initially presented in the receptive filed, then the saccade moved the receptive field away from the target location. The activity of these neurons decreased after the saccade.

The results of all experiments described in this section support the conclusion that reach plan-encoding neurons within the PRR update their representation of the remembered target after a saccade.

Example 6

Reconstructing the Reach Target Location of a Planned Reach

The reconstruction process involves estimating the target location given a finite set of observed neural activity. The estimate may be used by a prosthetic controlling device. In order to accurately reconstruct the planned reach target location, several existing and novel reconstruction algorithms may be used. These algorithms include neural net approaches (Salinas and Abbott 1994 J. Comput. Neurosci. 1: 89–107; Salinas and Abbott 1995 J. Neurosci. 15: 6461–6474; Lukashin et al 1996 NeuroReport 7: 2597–2601), a Kalman filter approach (Brown et al 1998 J. Neurosci. 18: 7411–7425), and a Bayesian approach (Zhang et al 1998 J. Neurophysiol. 79: 1017–1044).

A published Bayesian reconstruction algorithm was applied to signals recorded from a population of PRR neurons (Zhang et al 1998 J. Neurophysiol. 79: 1017–1044).

Expressed mathematically, the Bayes rule may be written as:

$$P(x|n)P(n)=P(n|x)P(x)$$

Where x is a vector representing the actual planned reach target location and n is a vector representing the number of spikes each neuron in the ensemble generated in some time interval. We wish to compute P(x ½ n), the probability that the planned reach target location is to a particular point, given the number of spikes observed across the population of neurons. The probability P(n) for the number of spikes n to occur can be determined by normalization and the probability P(x) that the planned reach target location is any particular location is uniform in this experimental design.

The critical step is to evaluate the conditional probability P(n ½ x), which is the probability for the number of spikes n to occur given that we know a plan is formed to reach to a particular location x. This probability is determined by direct measurement of each PRR neuron's response when the monkey plans to, and then does, reach to x. With the additional assumptions that the spikes have Poisson distributions, which is easily verified and is typically true for cortical neurons, and that different PRR neurons are statistically independent, which we can eventually verify given simultaneous recordings, we obtain the expression:

$$P(n|x) = \prod_{i=1}^{N} P(n_i|x) = \prod_{i=1}^{N} \frac{(\tau f_i(x))^{n_i}}{n_i!} \exp(-\tau f_i(x))$$

Where fi(x) is the average spike rate of neuron i when planning a reach to x, and t is the length of the timeintegration window. The final expression used to reconstruct the planned arm movement is:

$$P(x|n) = C(\tau, n)P(x)\left(\prod_{i=1}^{N} f_i(x)^{n_i}\right)\exp\left(-\tau\sum_{i=1}^{N} f_i(x)\right)$$

Where C (t,n) is a normalization factor. The best estimate for the planned arm movement is simply the most probable x:

$$\hat{x} = \mathrm{argmax}_x P(x|n)$$

Figure 6A:
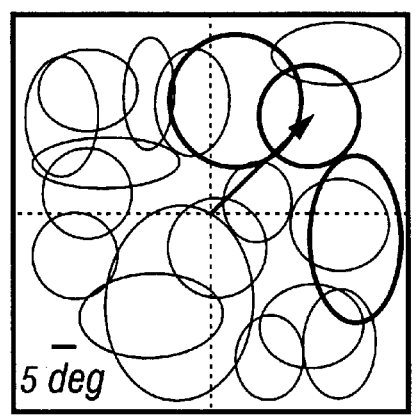
FIG. 6: A schematic representation of the reconstruction process for a hypothetical set of reach plan-encoding neurons, as described in Example 6, infra. A): The receptive fields are depicted as ellipses or circles that represent the response full-width at half-maximum contours. The actual planned arm movement is depicted as an arrow extending to a point in the first quadrant. B) The spike trains of three different identifiable neural signals are depicted (e.g., after spike sorting). C): The best estimate of the actual planned reach is depicted (e.g., the thick black arrow) which results from using various decoding algorithms.
Figure 6B:
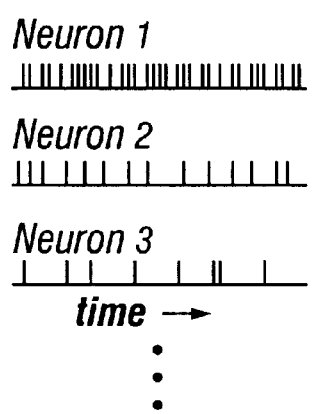
Figure 6C:
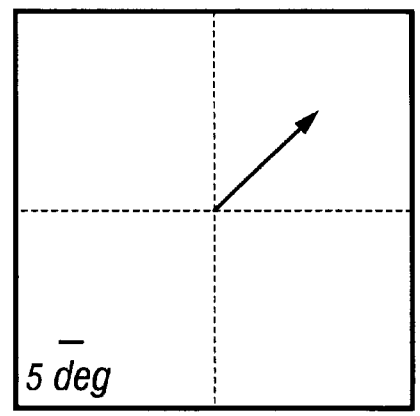

FIG. 6 shows a schematic representation of the reconstruction process for hypothetical reach plan-encoding neurons. For example, when a reach is planned up and to the right, many neurons will respond since the reach falls within these neurons' receptive fields. FIG. 6A shows ellipses or circles which represent the full-width at half maximum contours of the receptive fields of the hypothetical neurons. The actual planned arm movement is depicted as an arrow extending to a point in the first quadrant. FIG. 6B depicts spike trains of three of the identifiable neural signals (e.g., after spike sorting). FIG. 6C shows the best estimate (e.g., the thick black arrow) of the actual planned reach, using various decoding algorithms.

Figure 7:
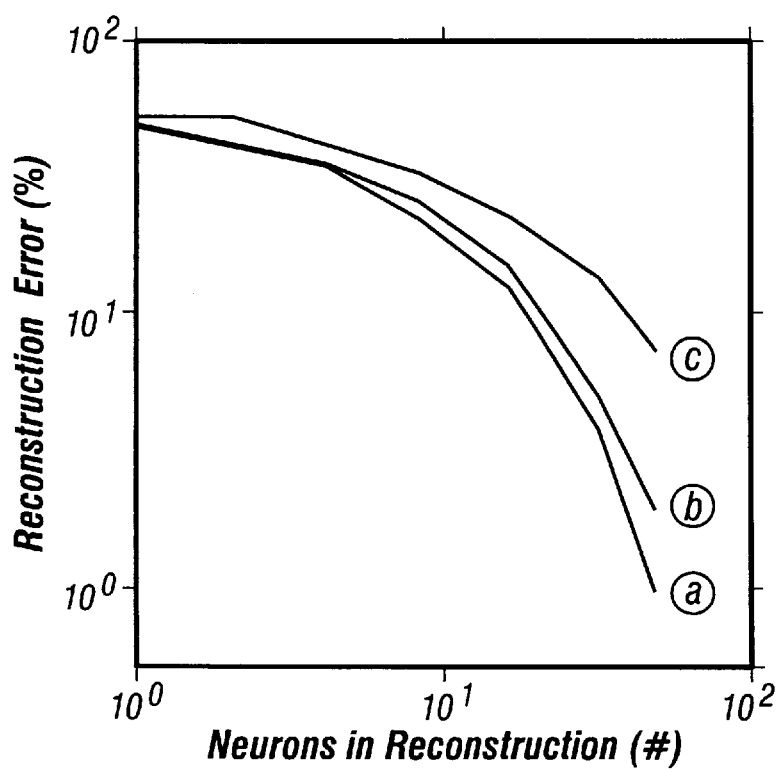
FIG. 7: Design curves generated by a Bayesian reconstruction algorithm to determine estimation accuracy of the planned reach location, as described in Example 6, infra.

Using this Bayesian reconstruction algorithm, we generated the design curves for three difference reaches, as shown in FIG. 7. Performance for up-left reaches (a), left reaches (b), and for down-left reaches (c) are shown. The number of neurons is plotted on the horizontal axis, and the planned arm-movement reconstruction error is plotted in the vertical axis. Monte Carlo simulations were performed for each neural ensemble size by selecting a reach direction, drawing a probabilistically representative set of spike counts (n; 50 times), and reconstructing the estimated planned reach direction using a Bayesian algorithm (Zhang, et al 1998 J. Neurophysiol. 79: 1017–1044). An ensemble of neurons of a particular size was selected from the total population of 49 neurons at random and with replacement; this selection was also repeated 50 times, for a total of 2500 reconstructions per data point. An error occurred if the reconstructed reach was more than one push button from the actual (Monte Carlo) planned reach direction. As expected, FIG. 7 shows that reconstruction performance improves with larger neural ensemble sizes, and error drops to a few percent with as few as 40 to 50 neurons. This is a worst case estimate because data were pooled from across recording days and we expect to do considerably better with simultaneously recorded data.

On average, the correct reach target location was predicted for 77% and 71% of Monte Carlo simulated trials (Baysian decode using 700 ms delay-period activity; 43 neurons for one monkey and 49 neurons for another). The performance was considerably better in some directions (98%, down for one monkey; and 86%, contralateral-up for another monkey) due to uneven sampling.

Example 7

A Neural Prosthetic

The present invention contemplates using a processed neural signal from a subject to directly instruct a desired action by the subject, wherein the desired action is a planned reach using the subject's natural arm or a reach device, such as a prosthetic limb device or a computer screen pointing device. The present invention further contemplates using the knowledge gained from reach plan-encoding neurons from monkeys (as described in Examples 1–6 above) to instruct a planned reach by a human subject, wherein the processed neural signals from the human subject are used to instruct the planned reach. The normal neural signaling pathway that directs a reach may be rerouted by using the processed neural signal to instruct a reach directly to the subject's arm or a reaching device.

Example 8

Sensory-motor Plasticity

When monkeys or humans first learn to use their mental plans to guide reaching movements, we expect these movements to be fairly accurate and to become even more refined with time. Using the signals from a subject's neurons, initial reaching accuracy is dependent upon the quality of the processed neural signal which depends in turn on the carefully measured reach tuning curves (see Examples 2 and 6). However, as a subject practices using a PRR-controlled prosthetic arm, we expect reaching accuracy to improve due to the modification of neural responses as a result of sensory/motor alterations or behavioral training (D M Clower et al. 1996 Nature 383: 618–621; Buonomano and Merzenich 1998 Annu. Rev. Neurosci. 21: 149–186). In the current context, visual-motor plasticity is expected to improve reaching accuracy by modifying reach tuning curves so as to guide the prosthetic arm to the target more accurately.

While neural plasticity is expected to improve reaching performance by altering neural responses, this assumes that the electronic system built to transform the neural signal into the processed neural signal is "hardwired" or fixed. In other words, neural plasticity will tend to change reach tuning curves so as to guide the prosthetic arm most accurately given the particular algorithm and parameters (i.e., Bayesian, see Example 6) used to estimate the desired reach target (e.g., processed neural signal). However, we expect that the use of adaptive algorithms will also improve reaching accuracy as adaptive algorithms can constantly optimize reaching performance by adjusting parameters and accounting for changes in the number and identity of neurons sampled (i.e., neural signals).

Together, neural and electronic adaptation is expected to provide the flexibility necessary for fine-tuning the relationship between desired, or planned reaching movement and the actual prosthetic limb movement.

Example 9

Introducing a Chronic Multi-sensor Array into the PRR of a Monkey

The following protocol describes the surgical procedure used to implant a multi-sensor array into the PRR of a 3.5 kg Rhesus monkey.

Pre-surgery

Administer Ketamine (0.3 ml) then Atropine (0.27 ml), both intramuscularly. Place arterial line for invasive blood-pressure monitoring. Then administer Buprenorphine (0.12 ml IM). Intravenously, administer Propofol (1–2 ml; 2.5 mg/kg) given slowly to effect. Intubate and start on Isoflurane. Give Cefazolin, 70 mg and Dexamethasone, 3.5 mg/0.88 ml, both intravenously. Start Mannitol drip (5 grams over 30 min/20 ml). Place second IV line and Heparin lock the line. Shave, scrub, and Bupivicaine block to surgery site. Place urinary collection system. Connect ECG, IBPM, NIBPM, end trial $CO_2$ and $O_2$ sat. Position the monkey with head up (30°) for good venous and CSF drainage. Note baseline $CO_2$, ECG, IBPM, NIBPM and O2 sat levels. Start ventilation and monitor CO2 levels. Lower CO2 to 28 when craniotomy occurs. Follow Mannitol with IV saline (10 ml/kg/hr). Prepare Lasix for use if indicated (7 mg/0.14 ml). Repeat Atropine if needed (0.27 ml). Repeat Buprenorphine at 6 hours post induction (0.12 ml). Repeat Cephazolin q4h (70 mg). Deep pain test. Place monkey in stereotaxic frame. Apply Opthane and paralube to both eyes. Scrub scalp and stereotax bars with iodine swabs. Mount "snake arms".

Surgery

Figure 8:
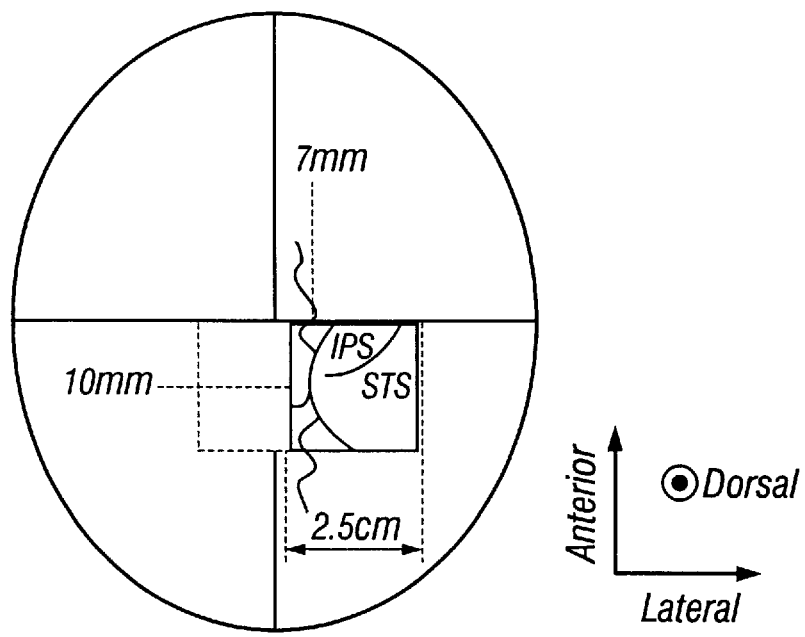
FIG. 8: The top view of a subject's skull and craniotomy, as described in Example 9, infra. The intraparietal sulcus (IPS) and superior temporal sulcus (STS) are shown.

Deep-pain test. Make a midline incision from posterior of brow to anterior of occipital ridge. Retract scalp laterally using gauze. Detach muscle attachments with elevators if needed. Clean skull with gauze and confirm that there is sufficient bone exposed to later build a head cap. Mount the stereotaxic arm. Mark the MRI-estimated PRR center (10 mm posterior, 7 mm lateral+stereotax offsets). Hall drill a 2–3 cm by 2–3 cm craniotomy centered on PRR (hall drill and burr bit; hall drill & side-cutting bit with foot plate). To avoid sinus, do not cut closer than 1–2 mm from the midline. See FIG. 8. Do irrigation and suction. Cut the dura on three sides (not medial side; using micro-scissors), separate dura from gray matter and reflect the flap medially with the pediole based on the sagittal sinus. Suture through the two corners on the dura and hang hemostats. Keep moist with gauze and saline. Open the arachnoid matter along the IPS, working anterior to posterior, while dissecting pial and arachnoidal vessels towards the lateral bank. Use a micronerve hook. Bioplar cautter as needed. Separate the sulcal walls microsurgically, using microelevators. Moisten the gauze covering the dura and apply antibiotics to cortex. Retract the sulcus:

1) Slightly bend spatula (size #17);
2) Clamp spatula to a snake arm;
3) Lower tip into the sulcus near the PRR target site;
4) Retract the lateral bank laterally;
5) Clamp snake arm in place and;
6) Repeat with second spatula/snake if needed.

Identify and mark target sites for the two percutaneous connectors. Both locations should be anterior of the craniotomy, allowing room for the head post. Shape the skull at these sites (hall drill and burr bit) so that the connectors will not slip during installation. Shape the dummy-array wire tethers such that the array sits in the sulcus and connectors sit at their sites. Shape the array(s) using the "plastic boxes in saline-filled box" kit. Fill the little boxes with sterile saline and include the aluminum weights.

1) Fill the large plastic box with sterile saline until the distance from the surface of the saline to the top of the little plastic boxes equals the distance from the top of cortex to the top of the skull.
2) Space the little plastic boxes, which support the percutaneous connectors, and the washer, which indicates the array position, according to the floorplan on the skull.
3) Include two "U" shaped bends in each wire tether for strain relief: one U shape below the dura and tangential to cortex and one within the silicone elastomer and perpendicular to cortex (sulcal bank).
4) Place strain relief bends in the reference wires (U shapes). Trim wires first if needed.
5) The wire tethers should rise out of cortex such that dura and the Precludea material (a W. L. Gore, Inc. product) can be easily sutured around the wires.
6) The wire tethers should arch up and over to the percutaneous connector sites without arcing above the final height of the silicone elastomer. Only silicone elastomer should contact the wire tethers. The wires should be several mm from the bone edge.
7) Grasp the two percutaneous connectors, move the system from the saline-kit to the brain, and lower the dummy array into the sulcus.
8) Position the reference wires such that the tips of the wires are close to the array. The wire tips should rest between cortex and dura (tips must not penetrate cortex).
9) Identify necessary corrections.
10) Return the array system to the saline kit.
11) Make necessary adjustments.
12) Confirm that the reference wires and the tethers are adjusted properly when the array is in the sulcus and the percutaneous connectors are at their target sites. Iterate adjustments until perfect.
13) Return the dummy array to the saline-kit.
14) Remove the insulation from the tips of the reference wires using a butane lighter flame.

Figure 9:
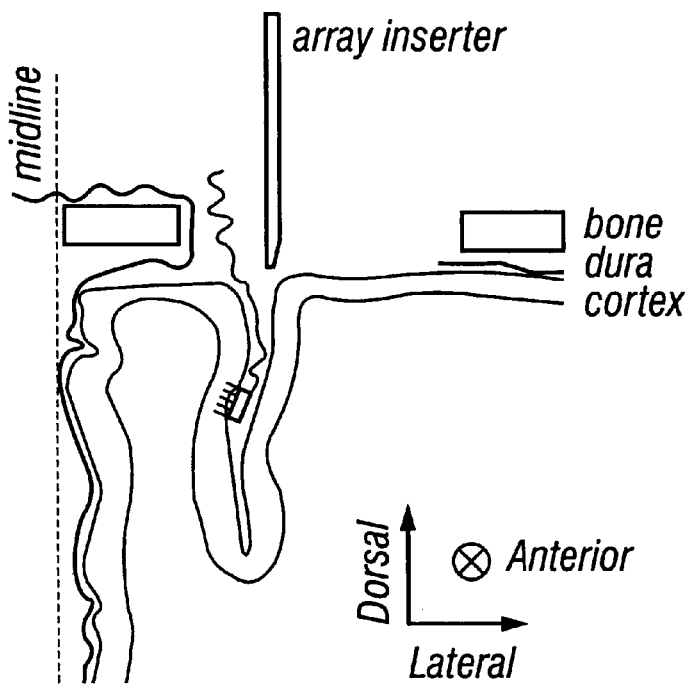
FIG. 9: A coronal view of the IPS with a silicon electrode array implanted in the PRR of a subject, as described in Example 9, infra.

With the dummy and percutaneous connectors in place, make final adjustments to wire paths. Mark the perimeter of the two percutaneous connectors with a pencil. Drill, thread and advance titanium bone screws into two holes located around each connector. Drill, thread and advance titanium bone (ground) screws into two holes located around the craniotomy. Do not place any screws within 2.0 cm anterior, or 2.0 cm posterior, of the array; this establishes an "MRI-safe corridor" for future coronal-section images. Return the dummy array system to the saline-box kit. Moisten the gauze covering the dura and apply antibiotics to cortex. Position the real array system next to the dummy system in the saline-kit (more blocks and washers). Shape the real array wires, including strain relief bends, so as to copy the dummy array wires. Secure sterile Microtek cables with towel clamps; connect Microtek cables to the array. Measure and record the impedance of each electrode in the array. Disconnect the Microtek cables from the Microtek connectors. Protect the medial bank of the IPS with Teflon (FEP) film. Lift the real-array system by the percutaneous connectors and move the assembly from the saline-kit to the sulcal area. Place the back side of the array on the retractor without touching PRR with the electrodes. Slide the array down the retractor, and into pre-implant position, by squirting saline on the retractor. Position the percutaneous connectors close to the previously marked target sites, allowing for the fact that the array is 1.0 mm (electrode length) form its final position. Adjust the wire tethers as needed while monitoring the array under the microscope. Confirm that the electrode array is in proper position: top edge 1–2 mm below the cortical surface; posterior edge just anterior to POS; and the electrode tips nearly touching the protective Teflon film. Confirm that the percutaneous connectors are positioned properly: sitting on the previously marked connector locations, near the bone screws. Mix methylmethacrylate (dental acrylic). Hold the percutaneous connectors. While monitoring the electrode array under the microscope, slide out the Teflon film. While monitoring the electrode array under the microscope, advance the array into cortex with the insertion tool. See FIG. 9.

Pack gel foam between the back of the array and the spatula. Evaluate need for leaving gel foam in place. Slide the percutaneous connectors approximately 1.0 mm medially to account for the new array position. Hold the percutaneous connectors. Methylmethacrylate the percutaneous connectors to the bone screws. Moisten the gauze covering the dura. Remove the sulcal retractor(s) by: S holding the spatula(s) and K releasing the snake clamps(s). Position the reference wires so that they lay between cortex and dura.

Secure sterile Microtek cables with towel clamps; connect Microtek cables to the array. Connect sterile ground cable from amplifier to ground screw. Measure and record the impedance of each electrode in the array. Monitor electrode signals with oscilloscope and speaker throughout surgery. Reapproximate the dura and mark where slits in the dura should be made to allow the wire tethers to exit without additional bending.

Figure 10:
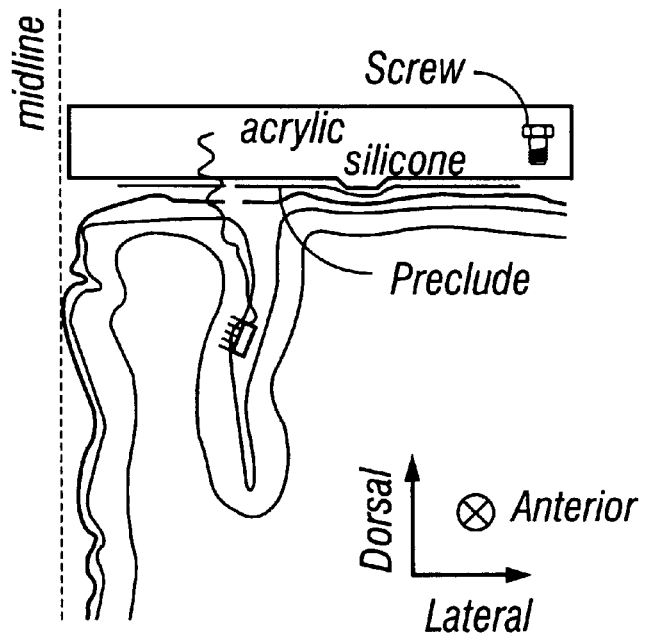
FIG. 10: A coronal view of the IPS and an electrode array implanted in the PRR of a subject, as described in Example 9, infra. The opening is closed with Preclude a silicone elastomer and methylmethacylate.

Do not disturb the wires/array. Slit dura as needed. Suture the dura closed around the perimeter and up the slits. Use Preclude artificial dura if needed. Size and cut the Preclude peritoneal material in order to cover the entire craniotomy, extending a few mm under the bone edge on all sides. Mark and slit the Preclude peritoneal material piece so that the wire tethers will not be bent or displaced when the Preclude material is placed. Slip the wire tethers up and along the slits, place the Preclude peritoneal material over the exposed dura, and tuck the Preclude under the skull along the craniotomy perimeter. See FIG. 10. Suture the Preclude peritoneal material slits. Mix the silicone elastomer. Fill in the craniotomy with silicone elastomer until about flush with the top of the skull. Totally encase the wires, working from the cortex end and moving toward the connector ends, with silicone elastomer. Place "+sign like ridges" on top surface of silicone elastomer. Turn on recovery room heat lamps. Drill, thread and advance titanium bone screws into at least four holes located around the craniotomy. Do not place any screws within 2.0 cm anterior, or 2.0 cm posterior, of the array. Mix methylmethacrylate. Build a "protective dome" over the craniotomy, including the percutaneous connector bases, with methylmethacrylate. Drill, thread and advance titanium bone screws into at least ten holes located around the skull. Mark the location of the head post and leave at least 2 cm between adjacent screws. Do not place any screws within 2.0 cm anterior, or 2.0 cm posterior, of the array. Place the head post, with cross-pin in place. Smear bone wax over all edges of the craniotomy protective dome. Build head cap using titanium screws, plastic-based head post, and methylmethacrylate.

Post-surgery

Carefully observe the monkey for many hours in recovery cage, in heated recovery room. Medicate as indicated for possible brain swelling. Standard course of post-op Buprenex, antibiotics and Dexamethason; divide dose down by one half each day.

Example 10

Testing the Chronic Multi-sensor Array

The stability of the multi-sensor array is currently being tested. The number of electrodes from which we can extract action potentials (functional electrodes) is approximately 10.

The change in each neuron's statistical waveform template over time will be quantified. The templates will be generated each day by recording several minutes of neural activity from each electrode while the monkey rests in the primate chair to monitor spontaneous neural activity. After the chronic electrode has stabilized, such that a known ensemble of neurons can be isolated for several days, the reach and saccade experiments discussed in Examples 1 through 5 above will be conducted.

Each neuron's receptive field will be characterized; the center of the receptive field will be mapped and the functional form of each receptive field will be determined. Once the eye-centered receptive field and eye-position gain field has been established for each neuron, the algorithms described previously in Example 6 may be used to calculate estimates for the location of the next reaching arm movement. In an experiment essentially identical to the one described above, the monkey will be instructed to reach for various targets (buttons) on the LED/push-button panel. The neural activity from all chronically-recorded neurons will be processed, off-line at first and eventually on-line, and the estimated reach target location will be compared to the real reach target location. Finally, we will train the monkey to move an animated limb displayed on a computer monitor using the reach plan read out from the reach plan-encoding neurons.

Example 11

Implementing the Algorithms

It is contemplated that algorithms can be implemented using existing commercial hardware (digital and analog). In the future, custom integrated circuits can be designed to reduce power, size and weight; this may allow the entire system to be implanted beneath the skin.

Figure 11:
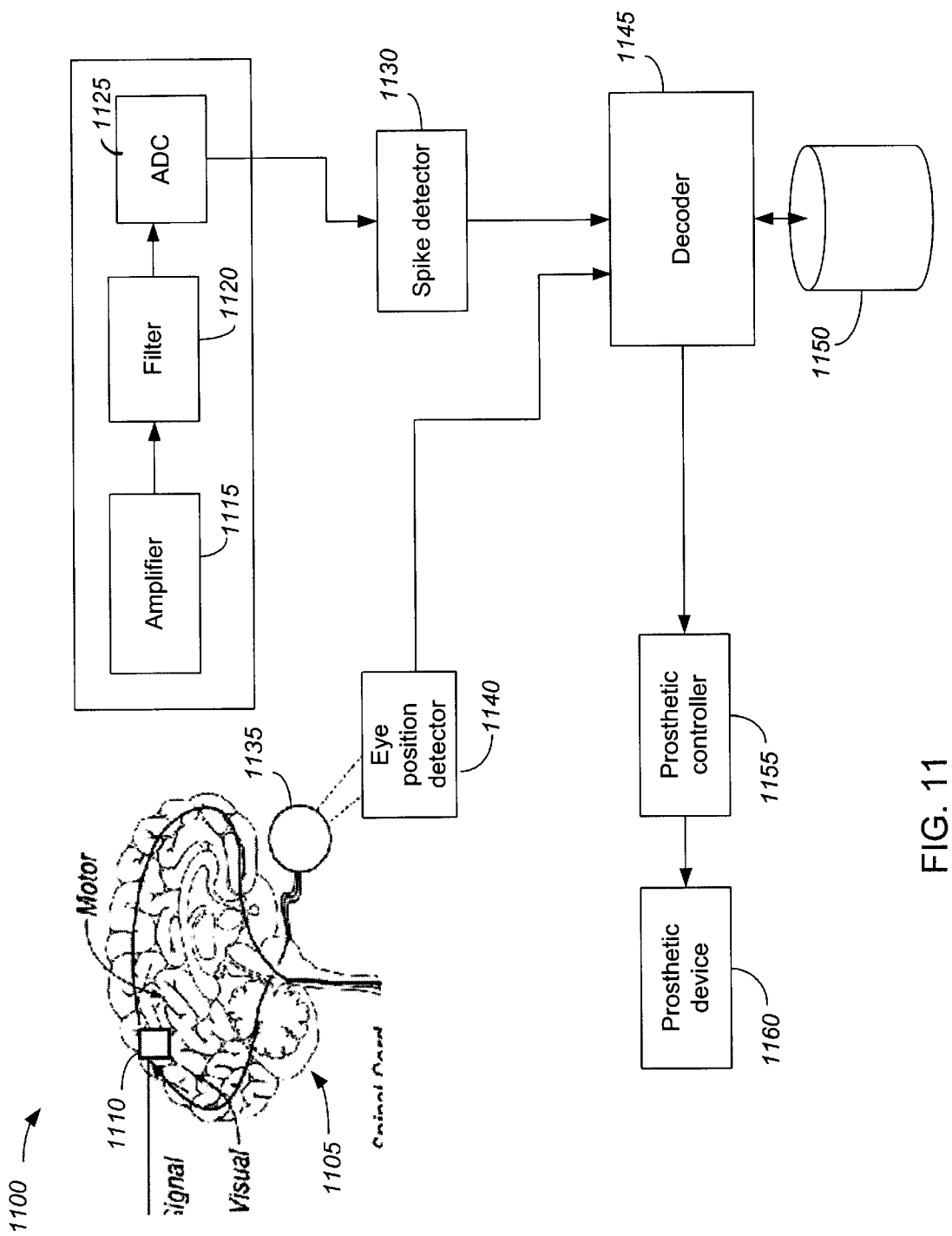
FIG. 11: A block diagram of an exemplary neural prosthetic system

FIG. 11 illustrates an exemplary neural prosthetic system 1100. The activity of neurons in the parietal reach region of a subject's brain 1105 may be recorded with an implant 1110. The implant 1110 may include an array of electrodes that measure the action potential of cells in their vicinity.

Neural activity measured with the implant 1110 may be amplified in one or more amplifier stages 1115, filtered by a filter 1120, and digitized by an analog-to-digital converter (ADC) 1125. The digitized signal may then be input to a spike detector 1130 which detects and sort spikes using known spike sorting operations.

The position of the subject's eye 1135 may be monitored with an eye position detector 1140. The spike train and eye position information may be input to a decoder 1145. The decoder 1145 may use characterized parameters of the selected neurons stored in a database 1150 to predict a reach plan.

The decoder 1145 may generate a high level signal indicative of the reach plan, including, e.g., target location and trajectory in an eye-centered, head-centered, or hand-centered frame of reference. The decoder 1145 may transmit this signal to a device controller 1155. The device controller 1155 may use the signal to control a prosthetic device 1160 to mimic the subject's intended movement. The output device may be, for example, a robotic limb, an animated limb or a pointing device on a display screen, or a functional electrical stimulation device implanted into the subject's muscles for direct stimulation and control.

A number of embodiments have been described. Nevertheless, it will be understood that various modifications may be made without departing from the spirit and scope of the invention. Accordingly, other embodiments are within the scope of the following claims.

What is claimed is:

1. Apparatus comprising:
   an input device operative to receive neural signals from a parietal reach region in a subject's brain;
   a signal processor coupled the input device and operative to generate a processed neural signal; and
   a decoder operative to generate a control signal indicative of a reach plan in response to said processed signal.

2. The apparatus of claim 1, wherein the reach plan comprises a trajectory.

3. The apparatus of claim 1, wherein the reach plan comprises a target location.

4. The apparatus of claim 1, wherein the neural signal encodes the reach plan in an eye-centered reference frame.

5. The apparatus of claim 1, further comprising an eye position detector operative to determine a position of an eye of the subject.

6. The apparatus of claim 5, wherein the decoder is operative to apply a gain modulation to the processed signal based on said eye position.

7. The apparatus of claim 5, wherein the decoder is further operative to generate a distributed representation of a target location in a head-centered reference frame using said eye-position.

8. The apparatus of claim 1, wherein the signal processor comprises:

an amplifier and a filter.

9. The apparatus of claim 1, wherein the signal processor comprises an analog-to-digital converter.

10. The apparatus of claim 1, wherein the signal processor is operative to determine a firing rate of one or more neurons in the parietal reach region.

11. The apparatus of claim 1, wherein the decoder comprises a database including characterized parameters of a neuron in the parietal reach region.

12. The apparatus of claim 11, wherein the characterized parameters include a receptive field of the neuron in an eye-centered reference frame.

13. The apparatus of claim 11, wherein the characterized parameters include an eye-position gain modulation associated with said neuron.

14. The apparatus of claim 1, wherein the input device comprises a neural implant.

15. A system comprising:

a neural implant operative to record neural signals from one or more neurons in a parietal reach region in a subject's brain;

a signal processor coupled the neural implant and operative to generate a processed neural signal;

a decoder operative to generate a control signal indicative of a reach plan in response to said processed signal; and a prosthetic device operative to execute a movement corresponding to the reach plan.

16. The system of claim 15, wherein the neural signal encodes the reach plan in an eye-centered reference frame.

17. The system of claim 15, further comprising an eye position detector operative to determine a position of an eye of the subject.

18. The system of claim 17, wherein the decoder is operative to apply a gain modulation to the processed signal based on said eye position.

19. The system of claim 17, wherein the decoder is further operative to generate a distributed representation of a target location in a head-centered reference frame using said eye-position.

20. The system of claim 15, wherein the prosthetic device comprises a prosthetic limb.

21. The system of claim 15, wherein the prosthetic device comprises a pointer device.

22. A method comprising:

measuring a neural signal from a parietal reach region in a subject's brain; and decoding a reach plan from said neural signal.

23. The method of claim 22, wherein said decoding the reach plan comprises decoding a target location.

24. The method of claim 22, wherein said decoding the reach plan comprises decoding a reach trajectory.

25. The method of claim 22, wherein said decoding comprises decoding a reach plan relative to an eye-centered reference frame of the subject.

26. The method of claim 22, wherein said measuring comprises recording a spike train from one or more parietal reach region neurons.

27. The method of claim 22, further comprising:

generating a control signal indicative of the reach plan.

28. The method of claim 22, controlling a prosthetic device to execute a movement corresponding to the reach plan with the control signal.

29. The method of claim 27, wherein the neural signal is represented in a form selected from a group consisting of electrical, chemical, magnetic, and blood flow.

30. The method of claim 22, further comprising:

determining a position of an eye of the subject.

31. The method of claim 22, further comprising:

applying a gain modulation to the measured neural signal based on said eye position.

32. The method of claim 30, further comprising:

generating a distributed representation of a target location in a head-centered reference frame using said eye-position.

33. An article comprising a machine-readable medium including machine-executable instructions, the instructions operative to cause the machine to:

measure a neural signal from a parietal reach region in a subject's brain; and decode a reach plan from said neural signal.

34. The article of claim 33, wherein the instructions operative to cause the machine to decode the reach plan include instructions operative to cause the machine to decode a target location.

35. The article of claim 33, wherein the instructions operative to cause the machine to decode the reach plan include instructions operative to cause the machine to decode a reach trajectory.

36. The article of claim 33, wherein the instructions operative to cause the machine to decode the reach plan include instructions operative to cause the machine to decode a reach plan relative to an eye-centered reference frame of the subject.

* * * * *